(12) United States Patent
McFetridge et al.

(10) Patent No.: US 9,821,013 B2
(45) Date of Patent: Nov. 21, 2017

(54) COMPOSITIONS AND METHODS FOR INDUCTION AND MODULATION OF ANGIOGENESIS AND METHODS AND ASSAYS FOR IDENTIFYING ANGIOGENESIS MODULATORS

(71) Applicant: UNIVERSITY OF FLORIDA RESEARCH FOUNDATION, INC., Gainesville, FL (US)

(72) Inventors: Peter S. McFetridge, Gainesville, FL (US); Marc C. Moore, Temple Terrace, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 276 days.

(21) Appl. No.: 14/243,123

(22) Filed: Apr. 2, 2014

(65) Prior Publication Data
US 2014/0294780 A1    Oct. 2, 2014

Related U.S. Application Data

(60) Provisional application No. 61/807,401, filed on Apr. 2, 2013.

(51) Int. Cl.
*A61K 35/50*    (2015.01)
*A61L 27/36*    (2006.01)
*C12N 5/071*    (2010.01)

(52) U.S. Cl.
CPC .......... *A61K 35/50* (2013.01); *A61L 27/3604* (2013.01); *C12N 5/069* (2013.01); *C12N 5/0691* (2013.01); *C12N 2502/1347* (2013.01); *C12N 2502/28* (2013.01); *C12N 2503/04* (2013.01); *C12N 2533/92* (2013.01)

(58) Field of Classification Search
None
See application file for complete search history.

(56) References Cited

U.S. PATENT DOCUMENTS

| | | | | |
|---|---|---|---|---|
| 4,829,000 | A * | 5/1989 | Kleinman | A61K 35/50 |
| | | | | 435/267 |
| 4,994,559 | A | 2/1991 | Moscatelli et al. | |
| 5,849,865 | A | 12/1998 | Cheng et al. | |
| 5,976,782 | A | 11/1999 | Parish et al. | |
| 7,163,681 | B2 | 1/2007 | Giles-Komar et al. | |
| 2002/0019350 | A1 | 1/2002 | Levine et al. | |
| 2005/0002915 | A1 | 1/2005 | Atala et al. | |
| 2005/0203636 | A1 | 9/2005 | McFetridge | |
| 2007/0071828 | A1* | 3/2007 | Tseng | A61K 35/48 |
| | | | | 424/528 |
| 2007/0128171 | A1 | 6/2007 | Tranquillo et al. | |
| 2008/0131522 | A1 | 6/2008 | Liu et al. | |
| 2009/0104164 | A1 | 4/2009 | Zhang et al. | |
| 2010/0226895 | A1* | 9/2010 | Boruch | A61K 35/30 |
| | | | | 424/93.7 |
| 2012/0129775 | A1 | 5/2012 | Zudaire et al. | |
| 2013/0195992 | A1 | 8/2013 | Tseng et al. | |
| 2014/0294780 | A1 | 10/2014 | McFetridge | |

FOREIGN PATENT DOCUMENTS

| | | |
|---|---|---|
| EP | 0218065 A2 | 4/1987 |
| EP | 0377855 | 11/1996 |
| KR | 20110025266 | 3/2011 |
| WO | WO03086373 | 10/2003 |

OTHER PUBLICATIONS

Gao et al "Mechanisms of action of angiogenin" Acta Biochim Biophys Sin (2008) vol. 40, Issue 7, pp. 619-624.*
Auerbach, R., Lewis, R., Shinners, B., Kubai, L. & Akhtar, N. Angiogenesis assays: a critical overview. Clinical chemistry 49, 32-40 (2003).
Auerbach, R., Akhtar, N., Lewis, R.L. & Shinners, B.L. Angiogenesis assays: problems and pitfalls. Cancer metastasis reviews 19, 167-172 (2000).
Bose, B. Burn wound dressing with human amniotic membrane. Annals of the Royal College of Surgeons of England 61, 444 (1979).
Burri, P.H. & Djonov, V. Intussusceptive angiogenesis—the alternative to capillary sprouting. Molecular aspects of medicine 23, S1-27 (2002).
Daniel, J., Abe, K. & McFetridge, P.S. Development of the human umbilical vein scaffold for cardiovascular tissue engineering applications. ASAIO J 51, 252-261 (2005).
Djonov, V., Baum, O. & Burri, P.H. Vascular remodeling by intussusceptive angiogenesis. Cell and tissue research 314, 107-117 (2003).
Epstein, S.E, Fuchs, S., Zhou, Y.F., Baffour, R. & Kornowski, R. Therapeutic interventions for enhancing collateral development by administration of growth factors: basic principles, early results and potential hazards. Cardiovascular Research 49, 532-542 (2001).
Febbraio, M., Hajjar, D.P. & Silverstein, R.L. CD36: a class B scavenger receptor involved in angiogenesis, atherosclerosis, inflammation, and lipid metabolism. Journal of Clinical Investigation 108, 785-791 (2001).
Ferrara, N. & Alitalo, K. Clinical applications of angiogenic growth factors and their inhibitors. Nature medicine 5 (1999).
Fett, J.W. et al. Isolation and characterization of angiogenin, an angiogenic protein from human carcinoma cells. Biochemistry 24, 5480-5486 (1985).
Folkman, J. Angiogenesis in cancer, vascular, rheumatoid and other disease. Nature medicine 1, 27-31 (1995).
Hariawala, M.D. et al. VEGF improves myocardial blood flow but produces EDRF-mediated hypotension in porcine hearts. Journal of Surgical Research 63, 77-82 (1996).
Iozzo, R.V. & San Antonio, J.D. Heparan sulfate proteoglycans: heavy hitters in the angiogenesis arena. Journal of Clinical Investigation 108, 349-355 (2001).

(Continued)

*Primary Examiner* — Allison Fox
(74) *Attorney, Agent, or Firm* — Thomas Horstemeyer, LLP

(57) ABSTRACT

The present disclosure provides methods and compositions, including a placental extract, for inducing and/or modulating angiogenesis; methods of identifying modulators of angiogenesis, and assays for identifying modulators of angiogenesis. The present disclosure also provides methods of making a composition, including a placental extract that can induce and/or modulate angiogenesis.

9 Claims, 10 Drawing Sheets

(56) References Cited

OTHER PUBLICATIONS

Jain, R.K., Schlenger, K., Hockel, M. & Yuan, F. Quantitative angiogenesis assays: progress and problems. Nature medicine 3, 1203-1208 (1997).
Jin, C.Z. et al. Human amniotic membrane as a delivery matrix for articular cartilage repair. Tissue engineering 13, 693-702 (2007).
Kalluri, R. Basement membranes: structure, assembly and role in tumour angiogenesis. Nature reviews. Cancer 3, 422-433 (2003).
Kleinman, H.K. & Martin, G.R. Matrigel: basement membrane matrix with biological activity. Seminars in cancer biology 15, 378-386 (2005).
Kurz, H., Burri, P.H. & Djonov, V.G. Angiogenesis and vascular remodeling by intussusception: from form to function. News in physiological sciences : an international journal of physiology produced jointly by the International Union of Physiological Sciences and the American Physiological Society 18, 65-70 (2003).
Laschke, M.W. et al. Angiogenesis in tissue engineering: breathing life into constructed tissue substitutes. Tissue engineering 12, 2093-2104 (2006).
Lawler, J. Thrombospondin-1 as an endogenous inhibitor of angiogenesis and tumor growth. J Cell Mol Med 6, 1-12 (2002).
Lee, S.-H. & Tseng, S. Amniotic membrane transplantation for persistent epithelial defects with ulceration. American journal of ophthalmology 123, 303-312 (1997).
Lee, R.J. et al. VEGF gene delivery to myocardium deleterious effects of unregulated expression. Circulation 102, 898-901 (2000).
Lokmic, Z. & Mitchell, G.M. Engineering the microcirculation. Tissue Eng Part B Rev 14, 87-103 (2008).
Montesano, R., Vassalli, J.-D., Baird, A., Guillemin, R. & Orci, L. Basic fibroblast growth factor induces angiogenesis in vitro. Proceedings of the National Academy of Sciences 83, 7297-7301 (1986).
O'Byrne, K.J., Dalgleish, A., Browning, M., Steward, W. & Harris, A. The relationship between angiogenesis and the immune response in carcinogenesis and the progression of malignant disease. European journal of cancer 36, 151-169 (2000).
Paslakis, G. et al. The Putative Role of Human Peritoneal Adipocytes in the Fight against Bacteria: Synthesis of the Antimicrobial Active Peptide DEFA1-3. Nephron Experimental Nephrology 115, e96-e100 (2010).
Pepper, M., Ferrara, N., Orci, L. & Montesano, R. Potent synergism between vascular endothelial growth factor and basic fibroblast growth factor in the induction of angiogenesis in vitro. Biochemical and biophysical research communications 189, 824-831 (1992).
Perretti, M. et al. Endogenous lipid-and peptide-derived anti-inflammatory pathways generated with glucocorticoid and aspirin treatment activate the lipoxin A4 receptor. Nature medicine 8, 1296-1302 (2002).
Risau, W. Mechanisms of angiogenesis. Nature 386, 671-674 (1997).
Rundhaug, J.E. Matrix metalloproteinases and angiogenesis. J Cell Mol Med 9, 267-285 (2005).
Kim, S., Bell, K., Mousa, S.A. & Varner, J.A. Regulation of Angiogenesis<i> in Vivo</i> by Ligation of Integrin α5β1 with the Central Cell-Binding Domain of Fibronectin. The American journal of pathology 156, 1345-1362 (2000).
Sullivan, D.C. & Bicknell, R. New molecular pathways in angiogenesis. British journal of cancer 89, 228-231 (2003).

Thurston, G., Murphy, T.J., Baluk, P., Lindsey, J.R. & McDonald, D.M. Angiogenesis in mice with chronic airway inflammation: strain-dependent differences. Am J Pathol 153, 1099-1112 (1998).
Vailhe, B., Vittet, D. & Feige, J.J. In vitro models of vasculogenesis and angiogenesis. Laboratory investigation; a journal of technical methods and pathology 81, 439-452 (2001).
Warren, M.S. et al. Comparative gene expression profiles of ABC transporters in brain microvessel endothelial cells and brain in five species including human. Pharmacological Research 59, 404-413 (2009).
Zisch, A.H., Lutolf, M.P. & Hubbell, J.A. Biopolymeric delivery matrices for angiogenic growth factors. Cardiovascular Pathology 12, 295-310 (2003).
Patarroyo, M., Tryggvason, K. & Virtanen, I. In Seminars in cancer biology, vol. 12 197-207 (Elsevier, 2002).
Xu, J. et al. Proteolytic exposure of a cryptic site within collagen type IV is required for angiogenesis and tumor growth in vivo. The Journal of cell biology 154, 1069-1080 (2001).
Adair, T. in Integrated systems physiology, from molecule to function to disease (Morgan & Claypool, 2011).
Wang, Y. & Zhao, S. in Vascular Biology of the Placenta (San Rafael (CA); 2010).
Cristofanilli, M., Charnsangavej, C. & Hortobagyi, G.N. Angiogenesis modulation in cancer research: novel clinical approaches. Nature reviews. Drug discovery 1, 415-426 (2002).
International Search Report from PCT/US2015/029666 dated Jul. 27, 2015.
International Search Report from PCT/US2014/032696 dated Aug. 27, 2014.
Thiex et al. "Tissue-specific cytokine release from human extraplacental membranes stimulated by lipopolysaccharide in a two-compartment tissue culture system." Reprod Bioi Endocrinol. Oct. 26, 2009 (Oct. 26, 2009), vol. 7, No. 117, pp. 1-10.
Miyagami et al. "Physiological changes in the pattern of placental gene expression early in the first trimester," Reprod Sci. Dec. 10, 2012 (Dec. 10, 2012), vol. 20, No. 6, pp. 710-714.
Presta et al. "Human placental tissue stimulates bovine capillary endothelial cell growth, migration and protease production." Biosci Rep. Sep. 1, 1985 (Sep. 1, 1985), vol. 5, No. 9, pp. 783-790.
Daniel et al. "Development of the Human Umbilical Vein Scaffold for Cardiovascular .Tissue Engineering Applications," ASAIO Journal, May 1, 2005 (May 1, 2005), vol. 51, pp. 252-261.
Hong et al. "The Effect of Human Placenta Extract in a Wound Healing Model", Annals of Plastic Surgery: Jul. 2010 vol. 65—Issue 1—pp. 96-100.
Pandolfi "A fully derived human placenta extract to induce the vascularization of engineered tissues" Politecnico Di Milano, Oct. 4, 2012; 135 pages.
European Supplementary Search Report for application No. EP14779851; dated Sep. 15, 2016, Examiner Sabine Novak-Giese; Munich, Germany; 8 pages.
William R. Prather, et al. "The role of placental-derived adherent stromal cell (PLX-PAD) in the treatment of critical limb ischemi"; Informa healthcare; Cytotherapy; 2009, vol. 11, No. 4, pp. 427-434.
Marc C. Moore, et al.; "Novel human-derived extracellular matrix induces in vitro and in vivo vascularization and inhibits fibrosis"; ScienceDirect, Biomaterials; 49, 2015, pp. 37-46.
Ma Kun, et al.; "Effect of Human Placental Extract on Proliferation of Human Umbilical Cord Blood CD34 + Cells In Vitro"; Journal of Experimental Hematology; 2012; 20(5), pp. 1183-1186.

* cited by examiner

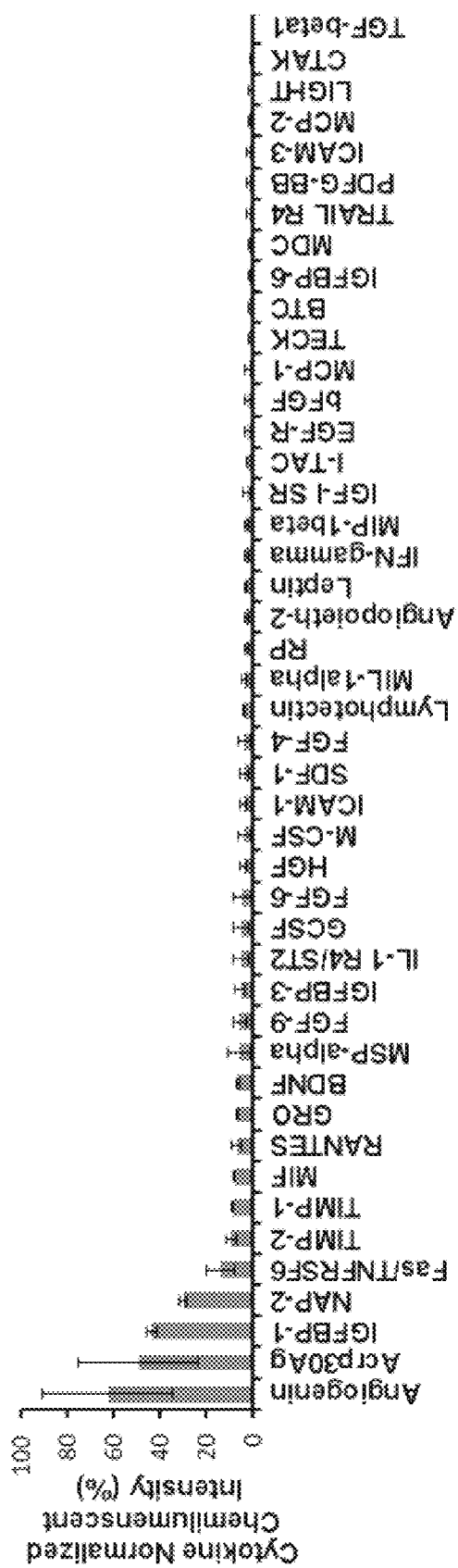
FIG. 2A
FIG. 2B
FIG. 2C

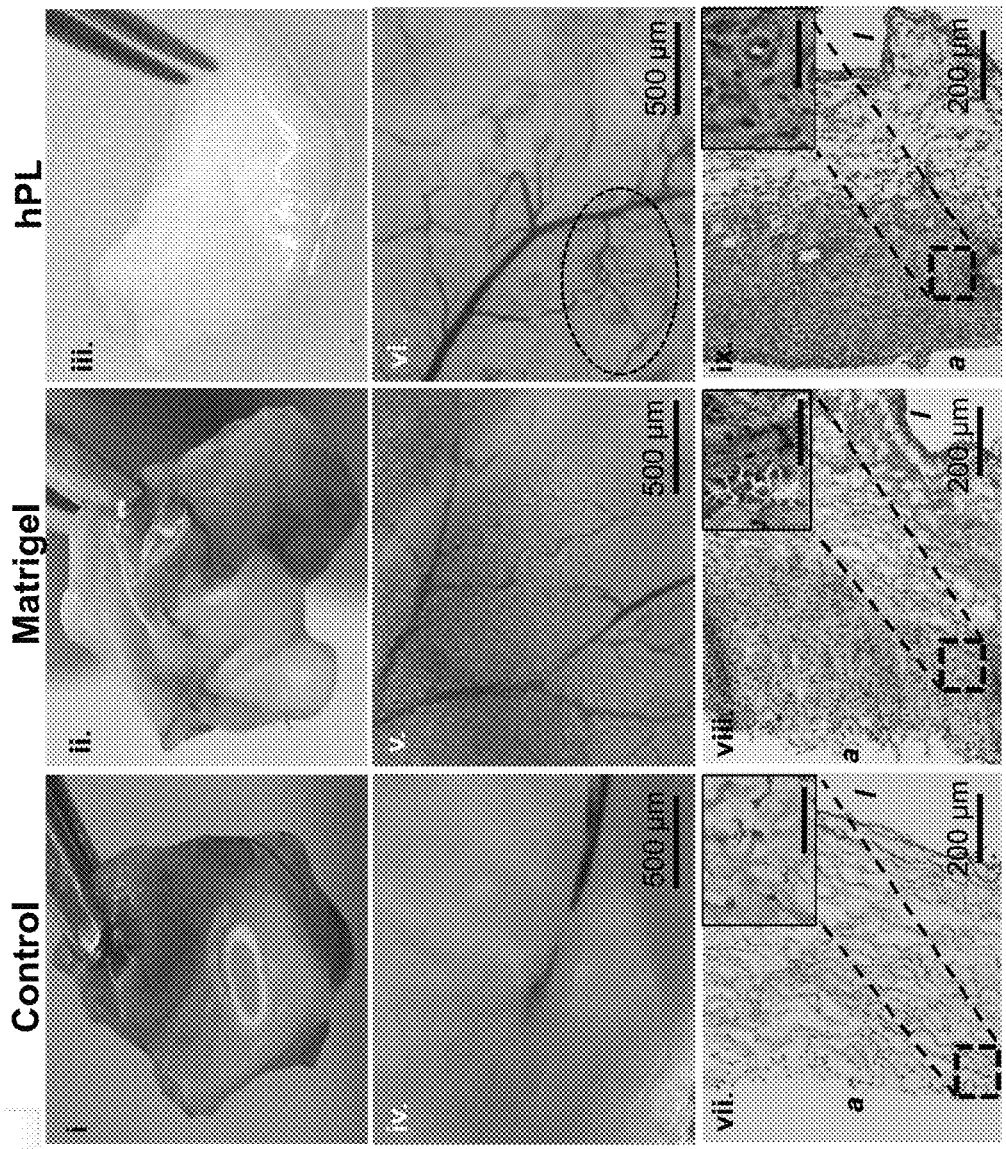
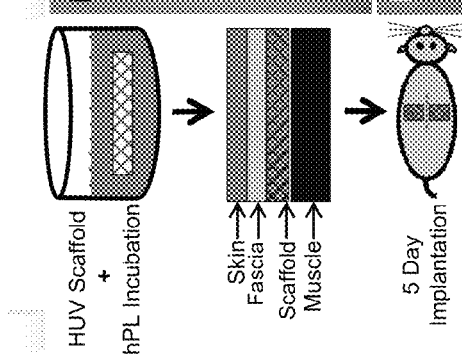

FIG. 7A
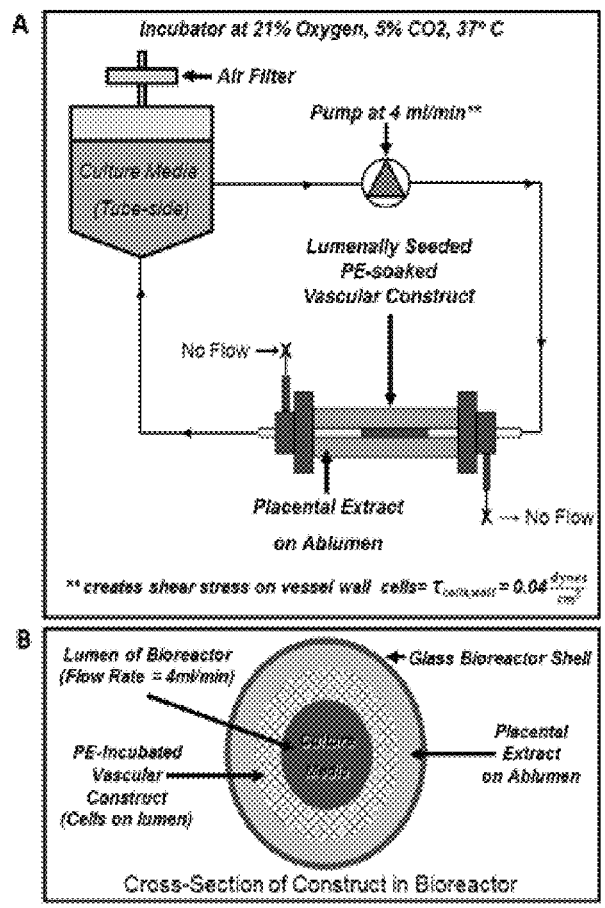
FIG. 7B
FIG. 7C
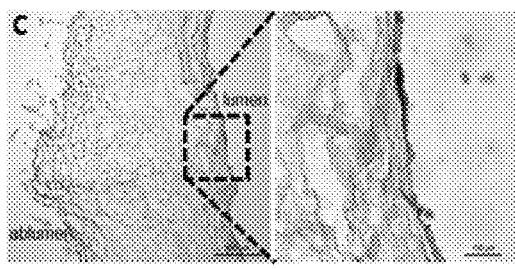
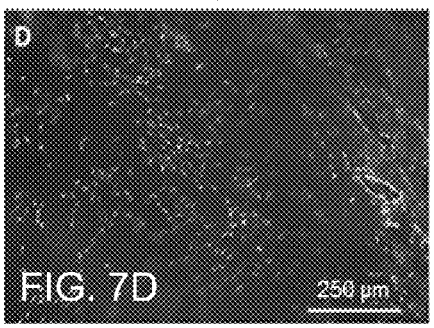
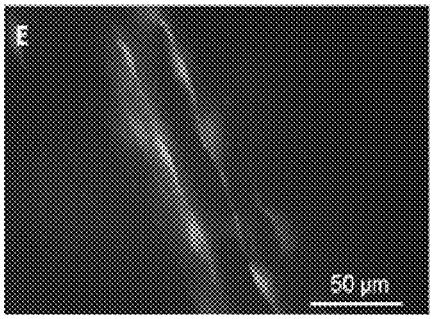
FIG. 7E

COMPOSITIONS AND METHODS FOR INDUCTION AND MODULATION OF ANGIOGENESIS AND METHODS AND ASSAYS FOR IDENTIFYING ANGIOGENESIS MODULATORS

CROSS-REFERENCE TO RELATED APPLICATIONS

This application claims priority to U.S. provisional applications entitled, "Compositions and Methods for Induction and Modulation of Angiogenesis and methods and Assays for Identifying Angiogenesis Modulators," having Ser. No. 61/807,401, filed on Apr. 2, 2013, which is entirely incorporated herein by reference.

STATEMENT REGARDING FEDERALLY SPONSORED RESEARCH OR DEVELOPMENT

This invention was made with Government support under grant number HL088207 awarded by the National Institutes Health. The Government has certain rights in this invention.

BACKGROUND

Angiogenesis enables the formation of blood vessels in physiological and pathological states ranging from wound healing to cancer. Angiogenesis modulation is both location and stimuli dependent, and each instance may involve a unique combination of regulatory molecules.

The inability to vascularize engineered organs and to revascularize areas of infarction has been a major roadblock to delivering successful regenerative medicine therapies to the clinic. The ability to modulate angiogenesis in a determinant fashion would have a significant impact in a wide range of clinical applications from defining normal and pathological vascular physiology, regeneration of tissues/organs, wound healing, infarct tissue repair and the inhibition of cancer. A variety of different approaches have been taken to initiate angiogenesis and drive larger vessel formation, including direct cell seeding (mono and co-cultures), use of stem cells, and combinations of human-derived modulators/growth factors. To date there has been little success translating these in vitro approaches, which typically use non-human animal compounds, to the clinic due to their discrete protein makeup, non-human derivation, tumor-derivation, or lack of genetic regulation in the case of methods to control gene expression.

Current methods to induce in vitro angiogenesis are made of simple combinations of human-derived modulators, use animal-derived stimulators, or are entirely dependent on the use of live animals for evaluation. Using these current in vitro models made of simple combinations of human-derived and/or animal derived modulators to test potential angiogenesis inhibiting drugs constrains the screening process because they fail to represent the broad set of human in vivo molecular interactions. Regulation of only selected molecular pathways also confines attempts to prevascularize engineered organs since modulating angiogenesis requires induction of many metabolic pathways. Also, currently, the most popular and successful approach employs Matrigel™, a material derived from Engelbreth-Holm-Swarm mouse sarcoma cells, which is considered inappropriate for human therapies. Thus, an improved human-based method to induce and modulate angiogenesis could spur both pharmaceutical development and regenerative medicine.

SUMMARY

Briefly described, embodiments of the present disclosure provide a human placental extract and methods of making a human placental extract, methods for inducing angiogenesis, methods for inducing vascularization of a biomaterial, implantable engineered biomaterials, and methods and assays for identifying modulators of angiogenesis.

Embodiments of the present disclosure for methods of making a human placental extract include first obtaining a sample from a human placenta and removing blood from the placental sample to produce a crude placental extract. The methods further include mixing the crude placental extract with a protein solubilization agent to solubilize proteins in the crude extract, separating solid materials from the solubilized protein-placental extract mixture, and performing dialysis on the solubilized protein-placental extract mixture to remove the protein solubilization agent from the mixture to produce the human placental extract.

The present disclosure also provides a composition including a human placental extract obtained from a human placental sample. Blood and solids have been substantially removed from the extract, and the extract comprises placental proteins including cytokines and growth factors, wherein the placental proteins were present in the placental sample.

In embodiments, the present disclosure includes a placental extract is made by removing blood from a sample obtained from the human placenta sample to produce a crude placental extract; mixing the crude placental extract with a protein solubilization agent to solubilize proteins in the crude extract; separating solid materials from the solubilized protein-placental extract mixture; and performing dialysis on the solubilized protein-placental extract mixture to remove the protein solubilization agent from the mixture to produce the human placental extract.

Embodiments of methods for inducing angiogenesis, in vitro (e.g., in cell culture) or in vivo, according to the present disclosure include growing endothelial cells in the presence of a human placental extract, where the placental extract was obtained from a human placenta sample that was treated to remove blood and solids, mixed with a protein solubilization agent, and dialyzed to remove the protein solubilization agent, and where the placental extract comprises placental proteins including cytokines and growth factors.

In embodiments, the present disclosure also includes methods for inducing vascularization of a biomaterial in vivo. In embodiments, such methods include implanting a biomaterial in a host, wherein, prior to implantation, the biomaterial was incubated in a human placental extract and wherein the human placental extract was obtained from a human placenta sample that was treated to remove blood and solids, mixed with a protein solubilization agent, and dialyzed to remove the protein solubilization agent, wherein the placental extract includes placental proteins including cytokines and growth factors.

The present disclosure also provides implantable engineered bioscaffolds including an engineered bioscaffold including a human derived substrate material incubated in a human placental extract. In embodiments the human placental extract is obtained from a human placenta sample that was processed to remove blood and solids, mixed with a protein solubilization agent, and dialyzed to remove the protein solubilization agent, and where the placental extract includes placental proteins including cytokines and growth factors.

In embodiments, the present disclosure provides methods for identifying an angiogenesis modulator, the method including growing a culture of human endothelial cells in the presence of a human placental extract obtained from a human placenta sample that was processed to remove blood and solids, mixed with a protein solubilization agent, and dialyzed to remove the protein solubilization agent, wherein the placental extract comprises placental proteins including cytokines and growth factors; contacting the human endothelial cell culture with a test compound; determining an amount of angiogenesis in the culture; and identifying the test compound as an angiogenesis modulator when the amount of angiogenesis in the cell culture is greater or less than the amount of angiogenesis is a culture growth in the absence of the test compound.

Embodiments of the present disclosure also include assays for screening test compounds to identify modulators of angiogenesis. In embodiments, the assays include a culture of endothelial cells grown in the presence of a human placental extract, where the placental extract was obtained from a human placenta sample that was processed to remove blood and solids, mixed with a protein solubilization agent, and dialyzed to remove the protein solubilization agent, where the placental extract includes placental proteins including cytokines and growth factors.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates Rhodamine Phalloidin ("red"—shown as grey branching pathways) and DAPI ("blue"—shown as lighter gray spots within branching pathways) showing branched cell filopodia during angiogenic sprouting after 1 day on placenta extract. FIG. 1B illustrates Rhodamine Phalloidin ("red"—shown as grey branching pathways) and DAPI ("blue"—shown as lighter gray spots within branching pathways) showing a maturing angiogenic network with extensive cell cording after 3 days. FIG. 1C shows Calcein ("green"—shown as grey branches) and DAPI ("blue"—shown as lighter grey spots within branches) stained HUVECs during the initial stages cell cording and angiogenic network formation after 1 day on placenta extract. FIG. 1D illustrates DAPI ("blue"—shown as grey dashed pathway) staining showing cell cording of HUVECS after 3 days on placenta extract. FIG. 1E illustrates HUVECs seeded onto a tissue culture plate at $4\times10^4$ cells/cm$^2$ and cultured in endothelial cell medium for 3 days. FIG. 1F illustrates formation of angiogenic networks by HUVECs seeded at $4\times10^4$ cells/cm$^2$ onto placenta extract that was adhered to the surface of a tissue culture plate at 100 µL PE/cm$^2$ and then cultured in endothelial cell medium for 3 days.

FIGS. 2A-2C illustrates biochemical analysis of hPE and genetic analysis of HUVECs seeded on hPE. FIG. 2A is a bar graph illustrating cytokines analysis as performed using a sandwich-based human angiogenesis antibody array; data was normalized on a scale ranging from negative control values (0%) to positive control values (100%) (data are representative of three biological replicates). FIGS. 2B and 2C are a bar graphs illustrating the normalized spectral abundance factor (%) of immune related (2B) and angiogenesis related (2C) BM related proteins as determined using LC-MS/MS. Fibrinogen normalized spectral abundance factor value is given as the sum of FGA and FGG values, and Laminin is given as the sum of LAMA2, LAMA4, LAMA5, LAMB1, LAMB2, LAMB3, and LAMC1 values.

FIG. 3A illustrates calcein stained HUVECS on hPE and Matrigel at variable cell seeding densities after 1 d, 3 d, and 5 d. The rate of angiogenic network maturation, defined as the time until maximum number of tubules/mm$^2$, was modulated in hPE samples by varying cell seeding densities. Quantitative analysis revealed that at 40,000 cells/cm$^2$ angiogenic networks took until day 3 to reach their maximum tubule density (tubules/mm$^2$), but at 80,000 cells/cm$^2$ networks reach their maximum tubule density in 1 day (data not shown). In matrigel samples, angiogenic networks were not well defined after day 1. Scale bars, 200 microns. FIG. 3B illustrates that WPMY-1 myofibroblasts did not have angiogenic formations when seeded on placenta extract (4B.i) but did when seeded on Matrigel (4B.ii).

FIG. 4A illustrates HUVECS seeded onto hPE, Matrigel, and control culture flasks (not coated) for 1 day with TSP-1 added to the culture media were then stained using Calcein AM. Scale Bars a, 200 µm. The graph of FIG. 4B shows, in hPE-coated flasks, mean total tubule length [mm] and mean number of branch points both decreased linearly with increasing TSP-1 concentrations. The graph of FIG. 4C illustrates a comparison of normalized percent reduction of angiogenic network coverage area; hPE-coated culture plates had significantly higher sensitivity to TSP-1 concentration than Matrigel-coated culture plates, with $R^2$ valuesbeing 0.97 and 0.36, respectively.

FIG. 5A is a schematic drawing illustrating placental derived cells, scaffolds, and cytokines, to induce angiogenesis in vitro in a hPE-soaked (human umbilical vein) bioscaffold after seeding and culturing for 3 days. FIG. 5B illustrates HUVEC seeded tissue scaffolds without hPE soaking did not form angiogenic networks. FIG. 5C shows a series of representative images of hPE-soaked bioscaffolds illustrating occurrences of both sprouting and intussusceptive mechanisms of angiogenesis after 3 days of culture. At a HUVEC cell seeding density of 20,000 cells/cm$^2$ sprouting angiogenesis was most prevalent (FIGS. 5C.i.-5C.ii.). At a seeding density of 40,000 cells/cm$^2$, occurrences of both sprouting and intussusceptive angiogenesis were observed (FIGS. 5C.iii.-5C.iv.), whereas at a density of 60,000 cells/cm$^2$ (FIGS. 5C.v.-5C.vi.) angiogenic tubules formed via intussusception.

FIGS. 6A-6B represent illustrations of in vivo angiogenesis in hPE-incubated bioscaffolds. FIG. 6A is a schematic drawing illustrating decellularized HUV scaffolds incubated in PE, Matrigel, or phosphate buffered saline (control) for 2 hr prior to implantation into a rat model between the fascia and muscle layers. FIG. 6B shows a series of images illustrating scaffolds removed for analysis after 5 d implantation. Significantly more fibrotic capsule formation occurred in control and Matrigel-incubated bioscaffolds in comparison to hPE incubated scaffolds (FIGS. 6B.i.-6B.iii.). Brightfield images taken through the frontal plane of the semi-translucent bioscaffold sheets show that in comparison to controls, Matrigel and hPE-incubated scaffolds (FIGS. 6B.iv.-6B.vi.) had significantly improved capillary network formation, with the most mature capillary beds in hPE scaffolds, showing formation of vascular structures with connected arteriole to capillary to venule blood flow (FIG. 6B.vi. (circled in dashed line)). Hematoxylin and Eosin staining revealed that hPE-incubated scaffolds (FIGS. 6B.vii.-6B.vi.) had the most scaffold remodeling in comparison to control and Matrigel scaffolds. Control scaffolds (FIG. 6B.vi.) had little remodeling of their original fiber orientation and also the least cell migration into the scaffold from the ablumenal surface of the HUV bioscaffold (indicated by italicized 'I'). Matrigel-incubated scaffold had slightly less cell migration from the ablumen surface of the HUV in comparison to hPE-scaffolds (FIGS. 6B.vii.-6B.ix.); when compared to controls, matrigel-incubated scaffolds also had less uniform cell distribution and less scaffold remodeling than hPE-incubated scaffolds, which had new collagen fiber orientation and a more uniform cell distribution.

FIGS. 7A-7E illustrate an embodiment for formation of angiogenic networks on human umbilical vein scaffolds (HUV) cultured using dynamic cell-culture conditions. As illustrated by the schematic drawings in FIGS. 7A and 7B, tubular HUV scaffolds were incubated in placenta extract for 2 hours before cell-seeding, and constructs were cultured for 5 days in a dual-perfusion bioreactor under standard cell culture conditions. Cells remained on the lumen of the scaffold and did not migrate (FIG. 7C). Cell-cording, an initial stage of tubule formation, was sporadic (FIGS. 7D and 7E).

DESCRIPTION

Figure 1A:
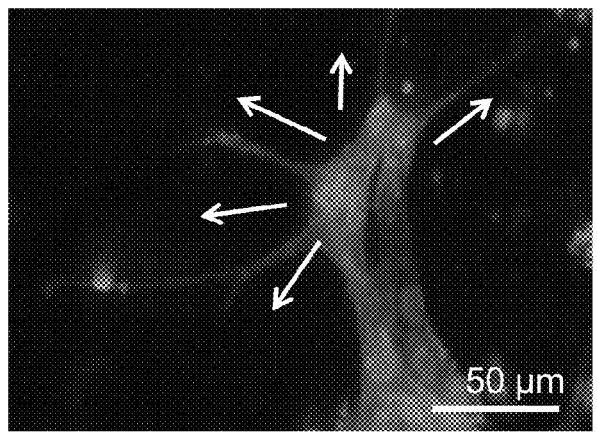
FIGS. 1A-1F illustrate the characterization of angiogenic networks formed on human placental extract (hPE).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, biochemistry, molecular biology, biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

Prior to describing the various embodiments, the following definitions are provided and should be used unless otherwise indicated.

DEFINITIONS

In describing the disclosed subject matter, the following terminology will be used in accordance with the definitions set forth below.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides, and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "gene" or "genes" as used herein refers to nucleic acid sequences (including both RNA or DNA) that encode genetic information for the synthesis of a whole RNA, a whole protein, or any portion of such whole RNA or whole protein. A "gene" typically refers to a hereditary unit corresponding to a sequence of DNA that occupies a specific location on a chromosome and that contains the genetic instruction for a characteristic(s) or trait(s) in an organism. The term "gene product" refers to RNAs or proteins that are encoded by the gene.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease. As used herein, the terms "prophylactically treat" or "prophylactically treating" refers completely, substantially, or partially preventing a disease/ condition or one or more symptoms thereof in a host. Similarly, "delaying the onset of a condition" can also be included in "prophylactically treating", and refers to the act of increasing the time before the actual onset of a condition in a patient that is predisposed to the condition.

By "administration" is meant introducing a compound of the present disclosure into a subject; it may also refer to the act of providing a composition of the present disclosure to a subject (e.g., by prescribing).

The term "organism," "subject," or "host" refers to any living entity in need of treatment, including humans, mammals (e.g., cats, dogs, horses, mice, rats, pigs, hogs, cows, and other cattle), birds (e.g., chickens), and other living species that are in need of treatment. In particular, the term "host" includes humans. As used herein, the term "human host" or "human subject" is generally used to refer to human hosts. In the present disclosure the term "host" typically refers to a human host, so when used alone in the present disclosure, the word "host" refers to a human host unless the context clearly indicates the intent to indicate a non-human host. Hosts that are "predisposed to" condition(s) can be defined as hosts that do not exhibit overt symptoms of one or more of these conditions but that are genetically, physiologically, or otherwise at risk of developing one or more of these conditions.

The term "expression," as used herein, describes the process undergone by a structural gene to produce a polypeptide. It is a combination of transcription and translation. Expression generally refers to the "expression" of a nucleic acid to produce a polypeptide, but it is also generally acceptable to refer to "expression" of a polypeptide, indicating that the polypeptide is being produced via expression of the corresponding nucleic acid.

"Angiogenesis" is a physiological process involving the growth of new blood vessels. Angiogenesis is an important part of biological processes, such as growth and development, wound healing, embryogenesis, and the like. Excessive angiogenesis can occur when diseased cells produce abnormal amounts of angiogenic growth factors, overwhelming the effects of natural angiogenesis inhibitors. Imbalances between the production of angiogenic growth factors and angiogenesis inhibitors can cause improperly regulated growth or suppression of vascular vessels. Angiogenesis-dependent or related diseases result when new blood vessels either grow excessively or insufficiently. The angiogenesis related disease can include diseases such as, but not limited to, cancer, precancerous tissue, tumors, cardiac infarction, and stroke. Excessive angiogenesis can include: cancer, diabetic blindness, age-related macular degeneration, rheumatoid arthritis, psoriasis, and more than 70 other conditions. Insufficient angiogenesis can include: coronary artery disease, stroke, and delayed wound healing, and is also a factor in tissue engineering as discussed in greater detail in the present disclosure.

As used herein, the term "modulate" and/or "modulator" generally refers to the act of directly or indirectly promoting/ activating/inducing/increasing or interfering with/inhibiting/ decreasing a specific function and/or trait in a cell/organism. In some instances a modulator may increase or decrease a certain activity or function relative to its natural state or relative to the average level of activity that would generally be expected. Modulation includes causing the overexpression or underexpression of a peptide (e.g., by acting to upregulate or downregulate expression of the peptide), or it may directly interact with the subject peptide to increase and/or decrease activity. Modulation also includes causing the increase or decrease of a specific biological activity or biological event, such as angiogenesis or biological events related to angiogenesis As used herein "upregulate" refers to the act of increasing the expression and/or activity of a protein or other gene product. "Downregulation" refers to decreasing the expression and/or activity of a protein or other gene product.

The term "isolated cell or population of cells" as used herein refers to an isolated cell or plurality of cells excised from a tissue or grown in vitro by tissue culture techniques. The term "a cell or population of cells" may refer to isolated cells as described above or may also refer to cells in vivo in a tissue of an animal or human.

The term "tissue" generally refers to a grouping of cells organized to cooperatively carry out a biological function and/or serve a biological purpose, such as forming all or part of an organ in an organism (e.g., connective tissue, endothelial tissue). While a "tissue" generally includes a grouping of similar cells, or cells of all the same type, a tissue may also include cells of more than one type where the group of cells as a whole serve a common purpose.

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

The term "bioscaffold" refers to any biocompatible substrate (naturally derived or synthetic) with sufficient structural stability to support the growth of a living biological substance (e.g., living cells). In embodiments of the present disclosure the biocompatible scaffold material is a naturally derived substrate (e.g., procured from a living organism, but that may have undergone additional processing and treatment; or produced from materials derived from a natural source), such as, but not limited to decellularized human umbilical vein scaffolds, In embodiments, the bioscaffolds of the present disclosure have a three-dimensional structure (rather than a planer, 2-dimensional structure) to support three-dimensional growth of living cells.

As used herein, the term "biodegradable" refers to a material that, over time in a natural environment (e.g., within a living organism or living culture), dissolves, deteriorates, or otherwise degrades and loses its structure integrity and ceases to exist in its original structural form. In embodiments of the present disclosure, biodegradable materials dissolve/degrade over a period of time within a host organism.

As used herein, the term "engineered" indicates that the engineered object is created and/or altered by man. An engineered object may include naturally derived substances, but the object itself is altered in some way by human intervention and design.

As used herein the term "test compound" may include peptides, peptidomimetics, small molecules, nucleic acid sequences, or other compounds that may have an effect on a living cell or organism. In some embodiments the "test compound" may be a compound, such as a chemical or peptide that is suspected of having a modulating effect on a biological activity, function or response to another compound. For instance, in the present disclosure, a "test compound" may be a compound suspected of having a modulating effect on angiogenesis, such as increasing angiogenic activity, decreasing angiogenic activity, and/or modulating the effect of a different angiogenesis modulator.

As used herein, the term "removed" or "substantially removed" indicates that an amount of a substance or compound has been separated from another composition, but does not require that absolutely all traces of the removed substance be absent from the remaining composition, such that the removed substance is completely undetectable. For instance, if blood has been "removed" or "substantially removed" from a composition, this indicates that a substantial proportion of the blood in the composition has been removed, but that some blood or blood components might still be detected in trace amounts upon rigorous screening (e.g., "substantially removed" does not require that a composition be 100% free of the component that has been "removed"; instead, a composition or substance can be about 99% free, about 95% free, or about 90% free of the "removed" component, or any percentage or range within the exemplary percentages, given above).

Discussion

The embodiments of the present disclosure encompass methods and compositions for inducing angiogenesis and methods and compositions for modulating angiogenesis, and methods of making compositions for modulating angiogenesis. The present disclosure also includes methods of identifying modulators of angiogenesis and assays for identifying modulators of angiogenesis. Embodiments of the present disclosure further include methods and compositions for delivering compositions for modulating angiogenesis. In embodiments, the present disclosure includes a placental extract that can be used to induce and/or modulate angiogenesis in vitro and/or in vivo in a tissue construct and/or in natural tissue and methods and compositions for delivering a placental extract to cells in a tissue construct and/or natural tissue. The present disclosure also includes a placental extract that can be used in an assay to identify compounds that modulate angiogenesis. Furthermore, the present disclosure includes a composition of delivery vehicle loaded with placental extract for controlled release of the extract to in vivo or in vitro cell populations to induce angiogenesis.

Angiogenesis is a complex process that is both location and stimuli dependent, and in each instance the capacity to modulate these processes may involve a complex combination of regulatory molecules.[1,2] Control of vessel formation is further complicated by different mechanisms of formation, with the two most understood being intussusception and sprouting[3,4]. Intussusception is characterized by the insertion of interstitial cellular columns into the lumen of preexisting vessels[5], and sprouting is characterized by endothelial cells sprouting toward an angiogenic stimulus in tissue previously devoid of microvessels[6]. Many molecules have been found to modulate angiogenesis[7], with more likely to be discovered. This diversity of angiogenesis inducers has driven the continued search and development of angiogenesis modulators for use in studies of vascular development, drug screening, and regenerative medicine therapies.[8]

Conventional models to study angiogenesis use either animal-derived stimulators or are entirely dependent on the use of live animals for evaluation[9]. In vivo animal studies provide a more accurate model to compare the complexity of biomolecular pathways and mechanisms that occur during human blood vessel formation. Standard in vivo angiogenesis models include the rabbit corneal neovascularization assay, the in vivo/in vitro chick chorioallantoic membrane assay, and the rat mesentery window assay[10]. When possible, in vitro angiogenesis models are chosen to better control complex biological phenomena; however, this often limits studies to a limited number of molecular species, e.g., VEGF. The outcomes of using a single molecule (or several) for this complex cascade maybe limiting in itself, where a more complex or multifactorial 'mix' may be needed promote competent vascularization.

For in vitro angiogenesis models, the murine derived basement membrane matrix (BMM) or 'Matrigel' assay has been the preferred model, as it brings a degree of in vivo complexity to an in vitro model and results appear to be more comparable to in vivo results. It is not suitable for clinical use, however, due to its derivation from Engelbreth-Holm-Swarm (EHS) mouse sarcoma cells and that it requires the sacrifice of large numbers of animals[11]. A number of in vitro human-derived modulators have been used to model angiogenesis. Historically, these have been based on single modulators (FGF, TGF-β, VEGF) and lack the variety of cytokines and chemical gradients that are native in vivo[12]. Given interspecies differences associated with animal-derived models[13, 14] and the complexity of deriving multi-protein formulations from human recombinant proteins, a robust human derived approach (including a more complex mix of multiple proteins at near physiological ratios) would have significant impact for mechanistic studies, screening angiogenesis drugs and the potential to enhance the clinical translation of regenerative medicine therapies. In addition, the capacity to modulate the angiogenic process to represent the different mechanisms and stages of formation would provide an improved platform to characterize key molecules and molecular pathways during vascularization.

The present disclosure provides methods to induce and modulate of angiogenesis in vitro and in vivo. In addition to inducing in vitro and in vivo angiogenesis, this model enables modulation of the rate of microvessel network maturation as well as selectively modeling sprouting and intussusceptive angiogenesis. In vivo the human placental extract (PE) was shown to significantly enhance capillary formation while eliminating fibrosis using dosed collagen based bioscaffolds.

The present disclosure describes such methods to induce and modulate angiogenesis in vitro and in vivo using a complex set of tunable, fully-human biomolecules derived from the human placenta. The approach uses directed fractionation and separations techniques to derive a complex of active human biomolecules isolated from the human placenta. In addition to inducing and modulating in vitro angiogenesis and in vivo angiogenesis, the methods and compositions of the present disclosure enable modulation of the rate of microvessel network maturation as well as selectively modeling sprouting and intussusceptive angiogenesis. In embodiments, the methods and compounds of the present disclosure also induce and modulate angiogenesis in both polymeric and ex vivo derived tissue scaffolds. These methods enable modulation of the rate of microvessel network maturation. In vivo, the human placental extract of the present disclosure was shown to significantly enhance capillary formation while eliminating fibrosis using dosed collagen based bioscaffolds.

Sustained delivery of growth factors effecting angiogenesis is also a challenge facing successful modulation of angiogenesis to promote vascularization for tissue engineering approaches. The present disclosure also provides methods and compositions for controlled release of the compositions of the present disclosure for modulating angiogenesis both in vitro and in vivo.

Human Placental Extract

The present disclosure provides a composition and methods for induction and/or modulation of angiogenesis that includes a human placental extract (PE). In embodiments of the present disclosure, the PE is made by obtaining a sample from a human placenta, removing blood from the placental sample to produce a crude placental extract (crude PE), mixing the crude PE with urea or other protein solubilization agent to solubilize the proteins present in the extract, removing remaining solids from the crude extract; dialyzing the urea-placental extract mixture to remove a substantial amount of the urea from the mixture to produce the human PE.

In embodiments, the process to make the human PE is performed at temperatures between about −86° C. and about 5° C. In embodiments, the human placental extract is made at temperatures at or below about 4° C.

In embodiments, the process of removing blood from the placental sample to make a crude placental extract includes homogenizing the human placenta sample with a buffer, centrifuging the homogenized sample, and discarding the supernatant containing blood. This process can be repeated multiple times (e.g., 2, 3 or more times) until substantially all of the blood has been removed from the sample (e.g., the sample is about 99% free of blood, about 95% free of blood, about 90 percent free of blood, etc.) to produce a crude PE. In an embodiment, the buffer is a Sodium Chloride solution (NaCl).

In embodiments, the proteins in the crude placental extract are solubilized by mixing the crude placental extract with a protein solubilization agent. In embodiments, the protein solubilization agent can be any compound or mixture of compounds capable of solubilizing (e.g., denaturing) proteins without permanently destroying the proteins or otherwise permanently rendering them inactive (e.g., the solubilization should reversibly denature the proteins, such that the proteins are capable of refolding, such as upon removal of the protein solubilization agent). In embodiments the protein solubilization agent can be, but is not limited to, urea, guanidine-HCl, or other similar compounds. In embodiments, the protein solubilization agent is urea, and the crude extract is mixed with a urea composition by homogenizing the crude extract with urea. In embodiments, the urea is mixed with the crude extract for a period of time between about 12 and about 36 hours. In embodiments, the urea is mixed with the crude extract for about 24 hours. In embodiments the urea solution is a urea buffer having about 0.5M concentration of urea or greater. In embodiments, the urea is about 2M or greater, about 4M urea, or greater, up to about 15M. In embodiments, the urea solution can have a concentration of about 0.5M to about 15M. In other embodiments the protein solubilization agent is guanidine-HCl having a concentration of about 0.5M to about 15M. In embodiments the guanidine-HCL has a concentration of about 6M. Although the methods and compositions described below are described using urea as the solubilization agent, it is to be understood that other suitable solubilization agents, such as, but not limited to, those discussed above, can be substituted for urea.

In embodiments, after mixing with urea, or other protein solubilization agent, solids are removed from the solubilized protein-crude extract mixture (e.g., urea-crude extract mixture). In embodiments, the solids are removed by centrifuging the PE mixture and discarding the pellet (containing the solids). This step can be repeated multiple times. After removal of the solids, the PE mixture (e.g., the supernatant) is dialyzed to remove urea, or other protein solubilization agent, from the placental extract. In embodiments, the dialysis solution is TBS. In embodiments, the dialysis solution is changed after a period of time (e.g., 1 hour, 2 hours, 3 hours, etc.) and dialysis is repeated a number of times (e.g., 2, 3, 4, etc.) to remove substantially all urea from the PE (e.g., the placental extract is about 99% free of urea, about 95% free of urea, etc.). In embodiments, the PE may be centrifuged again to remove remaining solids (e.g., polymerized proteins, and the like). In embodiments, the remaining PE is a clear to pinkish viscous substance. Additional details about embodiments of the process of the present disclosure of making the placental extract of the present disclosure can be found in the Examples below.

Thus, embodiments of the present disclosure also include a PE made by the methods of the present disclosure. In embodiments, the present disclosure includes a PE made by removing blood from a sample obtained from a human placenta sample to produce a crude PE; mixing the crude placental extract with a protein solubilization agent (such as, but not limited to urea, guanidine-HCl, etc.) to solubilize proteins in the crude extract; separating solid materials from the solubilized protein-PE mixture; and performing dialysis on the PE mixture to remove the protein solubilization agent (e.g., urea) from the mixture to produce the human PE.

The present disclosure thus includes a human placental extract including an extract obtained from a human placenta (e.g., from a human placental sample) having the blood and solids substantially removed and retaining (some or all) of the placental proteins that were present in the placental sample. In embodiments, the placental proteins include cytokines and growth factors.

Analysis of the PE of the present disclosure reveals that the PE includes many proteins including many cytokines and growth factors. In embodiments of the placental extract of the present disclosure, the extract includes at least 20 different cytokines. In some embodiments it contains up to 40 different cytokines. Other embodiments include at least 50 cytokines. Some cytokines that can be present in the PE of the present disclosure include those listed in the example below. For instance, some of the cytokines that can be present in the PE of the present disclosure include, but are not limited to, angiogenin, Acrp30Ag, IGFBP-1, NAP-2, and Fas/TNFGSF6, and RANTES, and MIF.

The cytokines and growth factors and other placental compounds present in the placental extract of the present disclosure can induce angiogenesis in a culture of endothelial cells, a tissue, a tissue construct, an engineered bioscaffold, and the like. The placental extract of the present disclosure can induce angiogenesis in vitro and in vivo. The placental extract of the present disclosure is capable of stimulating growth of endothelial cells. In embodiments the human PE of the present disclosure is capable of modulating angiogenesis. Compared to other conventional compounds used for inducing angiogenesis, such as BMM (compounds including single purified angiogenesis modulators (such as purified VEGF-alpha or SDF-1) and purified fibrin) the PE of the present disclosure stimulates increased angiogenic growth of endothelial cells (e.g., tubule and network formation) and decreased angiogenic-type growth of myofibroblasts (e.g., tubule formation) as compared to BMM. The PE of the present disclosure also stimulates different growth and/or differentiation patterns for various cell lines (e.g., stem cells, smooth muscle cells, etc.) as compared to BMM, such that the growth/differentiation patterns of such cells are distinguishable from growth with BMM.

The PE of the present disclosure is also capable of upregulation of various genes in endothelial cells in comparison to endothelial cells grown in the absence of the PE. Some such genes include angiogenesis related genes, extracellular matrix remodeling genes, and vascular development genes. Some angiogenesis related genes include, but are not limited to: ANGPTL4, CXCL3, human growth factor (HGF), ANGPT2, PGF, TYMP, VEGFA, HIF1A, and FGF1. Some extracellular matrix remodeling genes that can be induced by the placental extract of the present disclosure include, but are not limited to: MMP2, MMP9, COL4A3, and LAMA5. Vascular development genes include, but are not limited to: CDH2, HAND2, LECT1, and MDK.

Methods for Modulating Angiogenesis

The present disclosure also includes methods for inducing angiogenesis in a cell culture, wherein the method includes growing endothelial cells in the presence of a human placental extract of the present disclosure. In embodiments the cell culture is grown in the presence of a placental extract of the present disclosure obtained from a human placenta sample that was treated to remove blood and solids, mixed with urea, and dialyzed to remove urea, wherein the placental extract comprises placental proteins including cytokines and growth factors. In embodiments, the endothelial cells are human endothelial cells; in yet other embodiments, the cells are human umbilical vein endothelial cells (HUVECs). In embodiments of the methods of inducing angiogenesis in cell culture, the cells are seeded at a density of at least about 40,000 cells/cm$^2$. In embodiments they are seeded at a density of at least about 80,000 cells/cm$^2$. In embodiments, the cell cultures can be grown on a plate containing growth media and the placental extract of the present disclosure.

The present disclosure also include methods for inducing vascularization of a biomaterial in vivo including incubating a biomaterial in a composition including the human placental extract of the present disclosure and implanting the biomaterial in the host. In embodiments, the biomaterial includes naturally derived materials and/or cells. In embodiments the biomaterial includes an engineered bioscaffold including human derived substrate material. In embodiments, the engineered bioscaffold includes human umbilical vein scaffold. In embodiments the human umbilical vein scaffold is decellularized. In some embodiments, the biomaterial is seeded with endothelial cells, such as, but not limited to human endothelial cells (e.g., HUVECs). In embodiments of the present disclosure the biomaterial includes an engineered scaffolding material including a human umbilical vein scaffold seeded with HUVECs). In some embodiments, the HUVECs are seeded on the bioscaffold at a cell density of at least about 40,000 cells/cm$^2$. In embodiments they are seeded at a density of at least about 80,000 cells/cm$^2$. In embodiments the biomaterial is incubated in the placental extract for at least about 2 hours.

Vascularization of Biomaterials and Engineered Bioscaffolds

The present disclosure also includes methods of vascularizing biomaterials, including but not limited to, engineered biomaterials, naturally derived biomaterials, and other biomaterials to be implanted in a host. In addition to vascularization of biomaterials, treatment of biomaterials with the placental extract of the present disclosure can also be used to pre-treat biomaterials for use in-vivo to aid in bio-acceptance, reduce inflammation, reduce rejection and scarring, etc. Thus, the placental extract of the present disclosure and compositions including the placental extract of the present disclosure can be used to "dose" any number of biomaterials in order to improve the outcome of such implant.

The present disclosure also includes specifically engineered biomaterials, such as implantable, engineered bioscaffolds including a human derived substrate material incubated in a composition including a human placental extract of the present disclosure. The bioscaffolds of the present disclosure can be implanted in a mammal, such as a human. Bioscaffolds of the present disclosure can include any biomaterial suitable for implantation in a host. Examples of bioscaffolds for use in the present disclosure include, but are not limited to, engineered bioscaffolds including tissue, matrix materials, any number of naturally derived biomaterials, and the like. In embodiments, the bioscaffolds are 2D or 3D bioscaffolds. In embodiments, the bioscaffolds includes human derived substrate material. In embodiments, the bioscaffold includes decellularized human umbilical vein scaffold. In embodiments, the bioscaffold is seeded with cells, such as, but not limited to human cells, human endothelial cells (e.g., human umbilical vein endothelial cells (HUVECs)), stem cells, other pluripotent cells, and the like.

As described in the Examples below, the bioscaffolds of the present disclosure incubated in the placental extract of the present disclosure induce more vascularization (e.g., angiogenesis) and less fibrosis that bioscaffolds incubated in the angiogenesis inducing compound BMM or a control compound. The bioscaffolds incubated in the placental extract of the present disclosure also had a higher ratio of immune suppressive and pro-angiogenic positive macrophages (e.g., CD205(M2)) versus proinflammatory positive macrophages e.g., (CD86(M1)) as opposed to bioscaffolds incubated in BMM or a control.

Angiogenesis Screening Assays

Since the placental extract of the present disclosure induces angiogenesis in cell culture it provides a good assay for identifying and screening for angiogenesis modulators. Thus, the present disclosure also includes methods and assays for identifying angiogenesis modulators.

In embodiments, a method includes growing a culture of human endothelial cells in the presence of a compound including a human placental extract of the present disclosure and contacting the human endothelial cell culture with a test compound. Since the placental extract induces angiogenesis in the cell culture, if angiogenesis is less than or more than expected, the test compound can be identified as an angiogenesis modulator. Thus, the method also includes determining an amount of angiogenesis in the culture and identifying the test compound as an angiogenesis modulator when the amount of angiogenesis in the cell culture is greater or less than the amount of angiogenesis is a culture growth in the absence of the test compound. In embodiments an increase in the amount of angiogenesis relative to a culture grown in the absence of the test compound indicates the test compound induces angiogenesis. A decrease in the amount of angiogenesis relative to a culture grown in the absence of the test compound indicates the test compound inhibits angiogenesis. As described in the examples below, a screen of the compound Thrombospondin-1 (TSP-1) according to the methods of the present disclosure identified the compound as an inhibitor of angiogenesis. The present disclosure also provides assays for screening test compounds to identify modulators of angiogenesis including a culture of endothelial cells grown in the presence of a human placental extract of the present disclosure. The assays of the present disclosure can be used with the methods of the present disclosure to identify modulators of angiogenesis.

Additional details regarding the tests and methods of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Induction and Modulation of Angiogenesis in Ex Vivo Derived Bioscaffolds Using Placenta Derived Extracts Introduction The present example describes methods to induce vascularization using a complex human placental extract (PE). The PE is derived from the human placenta and is capable of inducing angiogenesis in 2D and 3D in vitro models, as well as in vivo within bioengineered tissue implants. This example also describes using the placental extract to positively screen thrombospondin-1 as an angiogenesis inhibiting protein with increased sensitivity relative to current in vitro models. Notably, this model allows for modulation over the rate and type (intussusceptive vs. sprouting) of angiogenesis and presents many advantages over conventional approaches as well as broad applications in the fields of regenerative medicine and pharmaceutics.

Mass transfer limitations within tissues represent one roadblock to producing effective biomaterials. Even if this can be temporarily overcome to allow improved cell migration within a human bioscaffold, the creation of an effective vasculature remains the primary goal to provide long-term nutrient delivery to thick, cell-dense materials. In adults, new blood vessels are predominately produced through the physiological process of angiogenesis,[47] which ultimately leads to the formation of nutrient rich vascular networks. The present example demonstrates that angiogenesis can be induced in a human umbilical vein (HUV) vascular graft and lead to a long-term nutrient delivery system.

The successful vascularization of engineered organs and the in vivo repair of infarct tissues through angiogenic modulators has been a major roadblock to delivering successful regenerative medicine therapies to the clinic. A variety of different approaches have been taken to initiate angiogenesis and drive larger vessel formation, including direct cell seeding (mono and co-cultures), stem cells, and combinations of human-derived modulators/growth factors. To date there has been little success in translating these in vitro approaches that typically use non-human animal compounds to the clinic.

A significant issue in the field is that the most popular/successful approach (Matrigel or Basement Membrane Matrix) is derived from Engelbreth-Holm-Swarm mouse sarcoma cells and as such is inappropriate for human therapies. Thus, an approach or mechanism using human-based materials—that actively promotes vessel formation both in in vitro and in vivo systems would have significant impact. The present example provides a human placenta extract (hPE) that is capable of inducing angiogenesis in 2D and 3D in vitro models, as well as in vivo within bioengineered tissue implants. The PE is a complex of active human biomolecules, and the present example demonstrates that, in addition to inducing in vivo and in vitro angiogenesis in the ex vivo derived human umbilical vein vascular graft, this model enables modulation over the rate and stage of angiogenesis. This example also demonstrates that the PE enhances capillary formation while also reducing fibrosis using dosed collagen based bioscaffolds.

Methods

Placental Extract Derivation.

Full-term placentas were collected from UF Health Shands Hospital (Gainesville, Fla.) within 12 hours of birth. The umbilical cords and fetal membranes were removed and the placenta was dissected into 2 cm cubes and frozen. 12 hours after progressive freezing to −86° C. at a rate of −1° C./min, the placental cubes were transported to a cold room maintained at 4° C. where the rest of the procedures were completed. Once at 4° C., 100 grams of the tissue was mixed with 150 mL cold 3.4 M NaCl buffer (198.5 g NaCl, 12.5 ml 2M tris, 1.5 g EDTA, and 0.25 g NEM in 1 L distilled water). The NaCl buffer/tissue mix was homogenized into a paste using a Tissuetek Homogenizer at 3200 RPM, then centrifuged at 7000 RPM for 15 minutes and separated from the supernatant. This NaCl washing process was repeated two additional times, discarding the supernatant each time to remove blood.

Next, the pellet was homogenized in 100 mL of 4M urea buffer (240 g urea, 6 g tris base, and 9 g NaCl in 1 L distilled water), stirred on a magnetic stirplate for 24 hours, and then centrifuged at 14000 RPM for 20 minutes (Sorvall RC6+ Centrifuge, Thermo Scientific, NC, USA). The supernatant was removed and dialysed using 8000 MW dialysis tubing (Spectrum Laboratories, Inc., CA, USA) placed in 1 L of TBS (6 g tris base and 9 g NaCl in 1 L distilled water) and 2.5 ml of chloroform for sterilization. The buffer was replaced with fresh TBS 4 more times, each at 2 hour intervals. Finally, contents of the dialysis tubes were centrifuged at 3000 RPM for 15 min (Allegra X-12R Centrifuge, Beckman Coulter, Inc., CA, USA) to remove polymerized proteins, and the supernatant (pink viscous lysate) was collected and stored at −86° C. until use.

Biomolecular Composition Analysis.

Relative cytokine levels were determined using a sandwich immunoassay array from RayBiotech, Inc. (Human Cytokine Antibody Array C Series 1000, Inc, GA, USA). Chemilumenescence was detected using a Foto/Analyst Luminaryfx Workstation (Fotodyne Incorporated, WI, USA) and the signal intensities were measured using TotalLab 100 software (Nonlinear Dynamics, Ltd, UK). The relative abundance of basement membrane biomolecules was performed by MSBioworks (Ann Arbor, Mich.) using nano LC/MS/MS with a Waters NanoAcquity HPEC (Waters, Milford, Mass.) system interfaced to a Orbitrap Velos Pro (ThermoFisher, Waltham, Mass.). Proteins were identified from primary sequence databases using Mascot database search engine (Boston, Mass.).

RT-PCR Analysis of Cells from hPL-Induced Angiogenic Networks.

Relative angiogenic gene expression was determined using 384-well RT$^2$ Human Angiogenesis RT$^2$ Profiler PCR Arrays (PANS-024A, Quiagen, CA, USA). ECs were detached from culture plates using Accutase (Innovative Cell Technologies, San Diego, Calif.) and immediately stored in 100 μl of RNA/ater. RNA was extracted using the RNeasy Mini Kit (Qiagen, CA, USA), and genomic DNA was digested using an RNase-Free DNase kit (Quiagen, CA, USA). Purified RNA was reverse transcribed to cDNA using the RT$^2$First Strand Kit (SA Biosciences, TX, USA) with incubation at 42° C. for 15 minutes followed by incubation at 95° C. for 5 minutes to stop the reaction. Next, cDNA was mixed with RT$^2$ SYBR Green Mastermix (SA Biosciences, TX, USA) and loaded into 384-well Human Angiogenesis PCR Arrays. Using the Bio Rad CFX384 Real-Time System (Bio-Rad, CA, USA) the loaded array plates went through a denaturization cycle for 10 min at 95° C., 40 cycles of 30 sec annealing/extension cycles at 60° C., and finally melting curves were obtained by ramping from 60° C. to 95° C. at a rate of ° C. per second. Data was analyzed the-using $\Delta\Delta C_t$ method and the RT$^2$ Profiler PCR Array Data Analysis Template v4.0 software package (Quiagen, CA, USA).

Human Umbilical Vein Endothelial Cell Isolation and Myofibroblast Cell Culture.

Endothelial cells were derived from human umbilical veins (collected from UF Health Shands Hospital, Gainesville, Fla.) by detachment from the vessels walls using a 1 mg/ml solution of bovine Type-I Collagenase in phosphate buffered saline (Gibco, Invitrogen, NY, USA). The primary derived human umbilical vein endothelial cells (HUVEC) were used between passages 1-3 for all experiments. For proliferation, cells were cultured using complete VascuLife Basal media (VascuLife VEGF Medium Complete Kit, Lifeline, MD, USA). For angiogenesis experiments, endothelial cell media was prepared using VascuLife Basal media with 25 ml of glutamine, 0.5 ml of hydrocortisone, 0.5 ml of ascorbic acid, 10 ml of FBS, and 1.25 μl of bFGF to 500 mL of (VascuLife VEGF Medium Complete Kit, Lifeline, MD, USA). Human myofibroblasts (CRL 2854) were used between passages 5 and 10 (ATCC, Manasses, Va.) and cultured using 10% FBS supplemented low-glucose DMEM.

Preparation of Placenta Extract-Derived Angiogenesis Assays.

Unless otherwise stated, 32 μl of placental extract was thawed and pipetted into each well of a 96 well plate. The extract was evenly coated onto the bottom of each well using an orbital shaker at 30 RPM for 1 minute. The coated plate was then incubated at 37° C. for 30 minutes. HUVEC were then plating by direct pipetting at 20000 cells/cm$^2$, 40000 cells/cm$^2$, or 80000 cells/cm$^2$. Multiple time points were investigated at each concentration including at days 1, 3, and 5. Thrombospondin-1 was tested as an angiogenesis inhibiting drug using final concentrations 0, 5, 10, 20, and 35 μg/μL diluted in endothelial cell media Morphological Characterization of Angiogenic Networks.

Network formation was analyzed after staining at a concentration of 2 μg/mL Calcein AM (Invitrogen-Life Technologies, NY, USA) with Endothelial cell culture media. In a dark room, dyed cells were incubated at 37° C., 5% $CO_2$ for 30 minutes, and then images were taken using a Zeiss Axiovert 200 inverted Fluorescence microscope (Zeiss, Thornwood, N.Y.). Images were analyzed to determine the tubule length, tubule width, branch points, and other meshwork characterizations using ImageJ 1.45s (NIH, Bethesda, Md.). Branch points were assigned manually as the positions at every node where branches meet or tubules sprout, and tubule length was assessed by determining the curve length from branch point to connected branch point. Tubule width measurements were carried out in three different zones per tubule, with two zones each 10 μm from the start and end and one zone in the middle of the curve length. The percent area of coveragewas determined by processing the images using the imageJ function "binary>>convert to mask" followed by measurement of the "mean." In TSP-1 experiments, final values were normalized to no dose samples, calculated as the percentage of "1" values relative to the total count of pixel values, and given as "% area coverage".

Human Umbilical Vein Scaffold Derivation and Placental Extract Incubation.

Placentas were collected from UF Health Shands HospitalFlorida (Gainesville, Fla.) and HUVs were dissected using an automated method as previously described.[32] Dissected HUV samples were decellularized in a 1% SDS (Thermo Scientific, Rockford, Ill.) solution at a solvent/tissue mass of 20:1 (w:v). Samples were decellularized on an orbital shaker plate at 100 rpm for 24 hours and then rinsed with PBS prior to incubation overnight at 37° C. in a 70 U/mL DNase I solution (Sigma-Aldrich, St. Louis, Mo.) in PBS. Sample were terminally sterilized using a 0.2% peracetic acid/4% ethanol (Sigma-Aldrich, St. Louis, Mo.) solution for 2 hours and finally pH balanced (7.4) using PBS. Following decellularization, scaffolds were cut into 1.5 cm×1.5 cm×0.075 cm sheets, prefrozen to −85 C, and then lyophilized using a Millrock bench top manifold freeze dryer (Kingston, N.Y.) for 24 hours at −85 C under 10 mT vacuum. Immediately prior to cell seeding, scaffolds were soaked for 2 hours in hPE, Matrigel, or PBS (control). and seeded.

Animal Implant Revascularization Study.

Male Sprague-Dawley rats (6 month old, 200 g) were purchased from Charles River Laboratories (Wilmington, Mass., USA), and all procedures were approved by the University of Florida IACUC (UF #201207728). In a biological hood, terminally sterilized HUV scaffolds were incubated for 2 hours in 5 mL of hPE, MATRIGEL, or PBS (control), respectively. Animals were anesthetized using isoflurane inhalation, and subcutaneous pockets were created on the left and right side of the back by blunt preparation with scissors. One scaffold was inserted into each subcutaneous pocket, and skin was sutured using 4-0 sutures (Coviden, Mansfield, Mass.). After 5 days implantation, animals were euthanized, and samples were removed for analysis.

To analyze capillary network formation, immediately after removal from the animal, fibrotic capsules were dissected with a scalpel and the HUV samples were placed onto glass slides. Top-down images of the semi-translucent scaffold sheets were taken using an Imager M2 light microscope (Zeiss, Oberkochen, Germany) with an Axiocam HRm digital camera (Zeiss, Oberkochen, Germany). To quantify cell migration and scaffold remodeling, tissue samples were embedded in Neg-50 frozen section medium, sectioned into 7 μm sections (Microm HM550 cryostat, Thermo Scientific, Waltham, Mass.), and stained using standard hematoxylin and eosin (H&E) staining (Richard-Alan Scientific, Kalamazoo, Mich.).

Statistics.

Results are reported as mean±standard deviation. Linear regression was performed using SPSS (IBM, Somers, N.Y.). Rt-PCR data was analyzed using $RT^2$ Profiler PCR Array Data Analysis Software v3.2 (SABiosciences, Valencia, Calif.).

Perfusion Bioreactor Culture and Angiogenesis Induction in the HUV Bioscaffold.

Cell-seeded tubular constructs were cultured in dual perfusion bioreactors (FIG. 7) for 5 days with a lumenal flow rate of 4 mL/min at 60 pulses/min. Shear stress on the vessel-wall was calculated using the Haagen-Poisseuille equation, under the assumptions that the flow of media is steady and laminar and the vessel is inelastic, cylindrical, and straight:[134]

$$\tau = 32 * \mu * \frac{Q}{\pi * d^3}$$

where Q is the mean volumetric flow rate and μ is equal to the kinetic viscosity of water at 37° C. (0.000692 kg/(m*s)).[134] The shear stress cycled from 0 dynes/cm² to 0.04 dynes/cm² during each pulse. The environment was maintained under standard cell culture conditions of 37° C. and 5% $CO_2$. Pressure within the system was maintained at negligible levels (<2 mmHg) in both the ablumenal and lumenal flow circuits resulting in no pressure gradient existed across the scaffold. Culture media in the bioreactor was replenished every two days. After 5 days of perfusion culture, the 10 cm long tubular scaffolds were dissected into ringlets for histological analysis.

Results

Derivation and Characterization of Human Placental Extract

After initial mechanical homogenization and centrifugation, the derivation technique utilized a urea step to linearize and solubilize molecules. This was followed by dialysis separations to remove urea and allow the biomolecules to refold into their original conformations. All steps of the derivation were performed in a cold room at 4° C. The final solution of PE was translucent, highly viscous, and consisted of biomolecules between 8 kD to 868 kD.

Figure 1B:
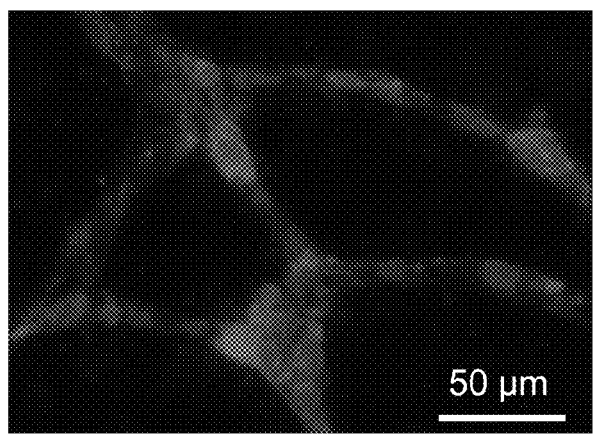
Figure 1C:
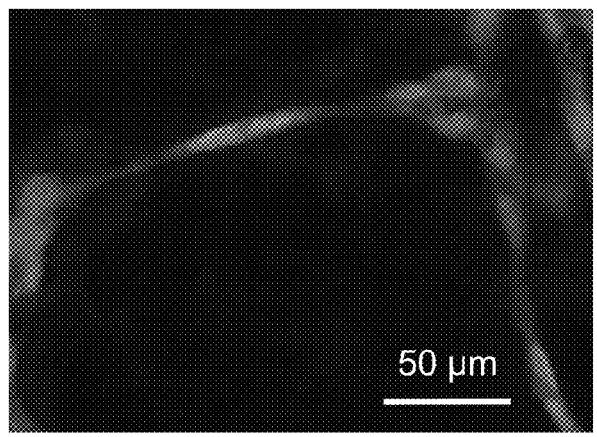
Figure 1D:
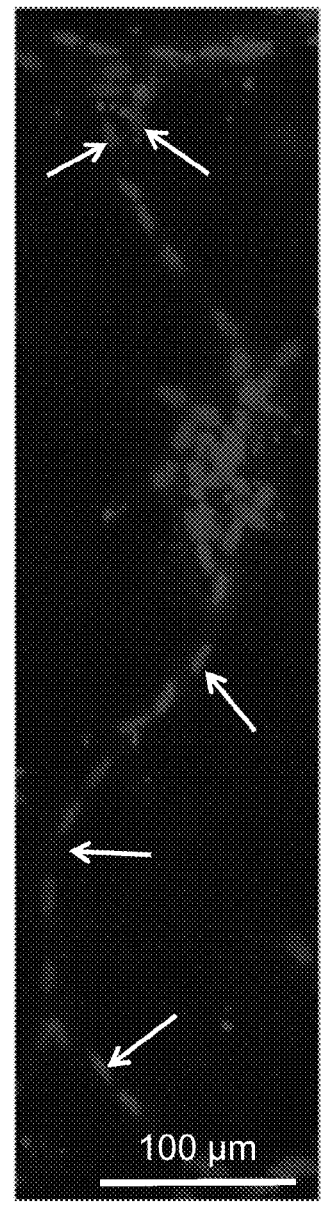
Figure 1E:
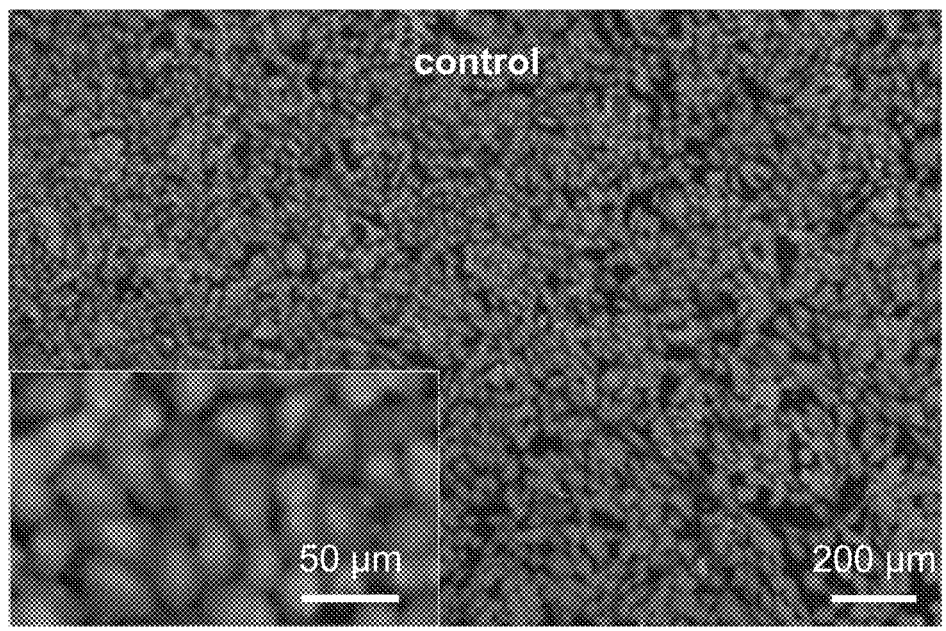
Figure 1F:
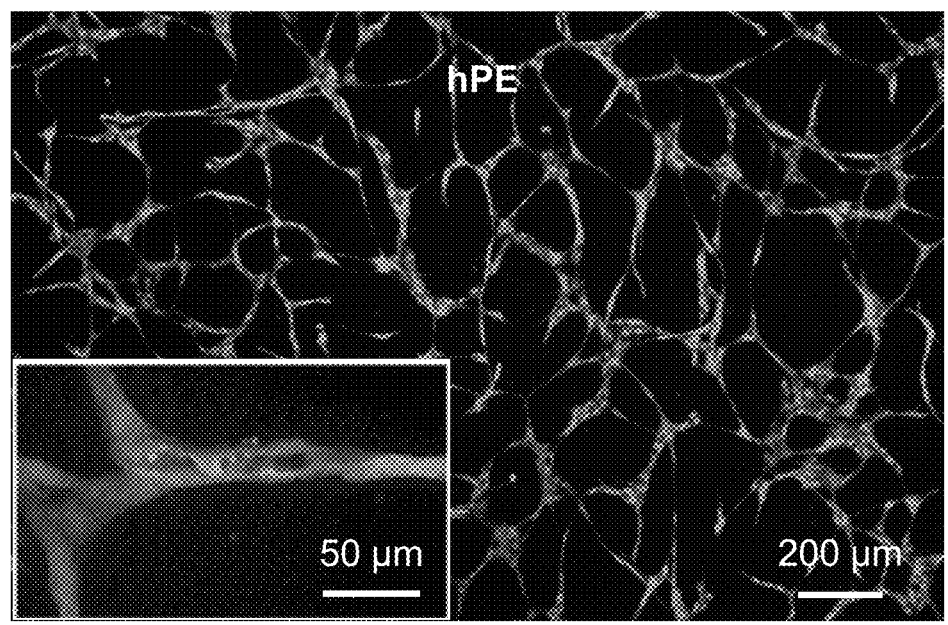

Angiogenic potential of the human placental extract (hPE) was initially characterized by seeding primary human umbilical vein endothelial cells (HUVEC) onto tissue culture plates (TCP) coated with the hPE. Early stage cell cording and sprouting were visible within 1 hour of cell seeding (data not shown), and angiogenic networks continued to mature until experimental termination at 3 d (FIG. 1A-B). The length of individual cell cords (multicellular) increased significantly from day 1 (FIG. 1C) to day 3 (FIG. 1D) of seeding. After 3 days of culture, cells had formed extensive angiogenic networks relative to control samples (FIG. 1E, 1F).

Biomolecular Characterization of Placental Extract

Figure 2D:
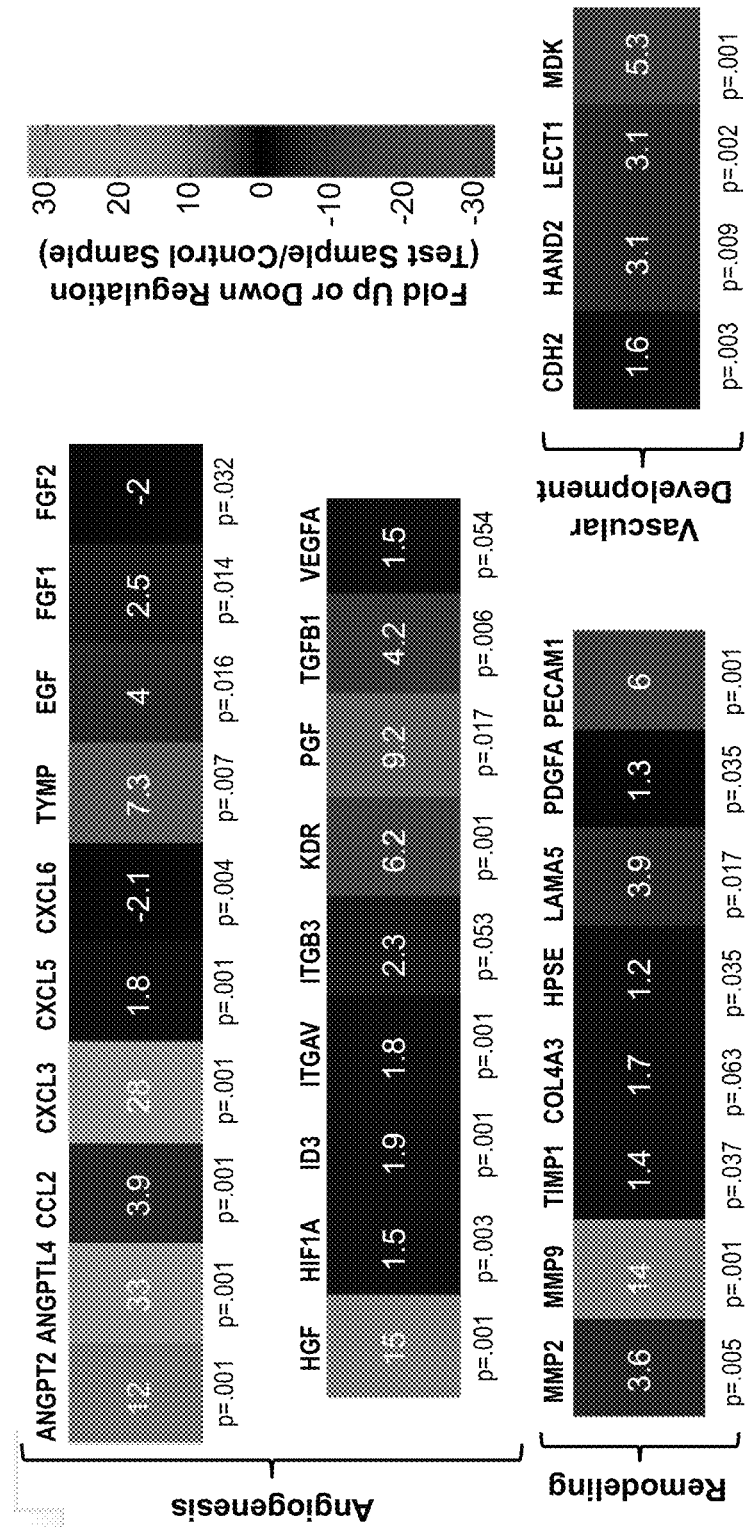
FIG. 2D illustrates genetic analysis performed on HUVECS seeded for 3 days onto 100 µL PE/cm$^2$ at a density of 80,000 cells/cm$^2$. Some angiogenesis related proteins not present in the lysate, including VEGFA, were upregulated by HUVECs when seeded onto hPE. Data are representative of four biological replicates. P-values are calculated using a Student's t-test of the replicate 2^(−Delta Ct) values for each gene in the control group and treatment groups.

Of the 120 cytokines assessed, 54 angiogenesis related cytokines were detected in the placental lysate (FIG. 2A). The most prevalent angiogenesis related chemokine was angiogenin, which is a potent stimulator of new blood vessel formation[16]. Significant pro-angiogenic chemokines including, but not limited to, hepatocyte growth factor (HGF), fibroblast growth factor-4 (FGF4), leptin (LEP), ICAM-1, ICAM-2 and TIMP-2 were also detected. LC-MS/MS showed the presence of immune-related proteins including annexins (ANXA1, ANXA2, ANXA4, and ANXA5), neutrophil defensin (DEFA1), interleukin enchacer-binding factors (ILF2 and ILF3), IL27, ITBG1, and MRC1. Angiogenesis related basement membrane (BM) proteins were also detected using lc-ms/ms, including laminin (LAMA2, LAMA4, LAMA5, LAMB1, LAMB2, LAMB3, and LAMC1), fibronectin (FN1), heparin sulfate (HSPG2) and type-4 collagen (COL4A1, COL4A2, and COL4A3), each of which has been shown to play key roles in angiogensis.[17-20]

Endothelial Cell Gene Expression within hPE-Induced Angiogenic Networks

In conjunction with chemokine analysis, HUVEC gene analysis further affirmed the angiogenic nature of placenta extract. RT-PCR analysis showed that endothelial cells seeded on hPE for 3 d expressed a wide range of essential pro-angiogenic genes including hepatocyte growth factor, epidermal growth factor, and placental growth factor (FIG. 2B). Additional upregulated genes include MMP2 and MMP9, which are proteolytic enzymes that aid in the degradation of the surrounding extracellular matrix in order to facilitate the migration of the endothelial cells as well as other cells associated with ECM remodeling[21]. Type IV collagen was also upregulated, which is associated with the formation of basement membranes in maturing microvessel systems[22].

Modulation of Capillary Development and Morphology In Vitro

Figure 3B:
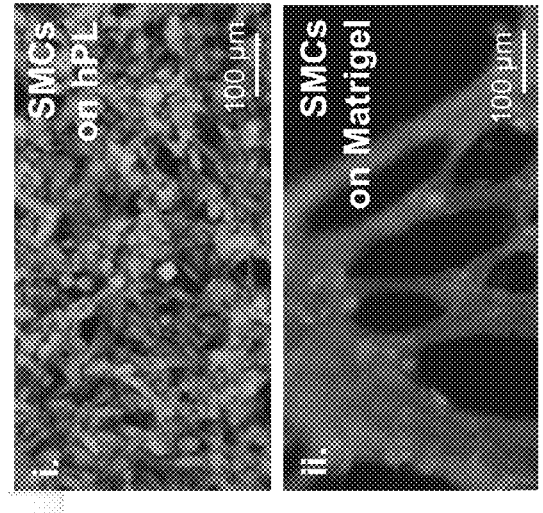
FIGS. 3A-3B illustrate in vitro angiogenic networks formed on hPE and matrigel coated tissue culture flasks.
Figure 3A:
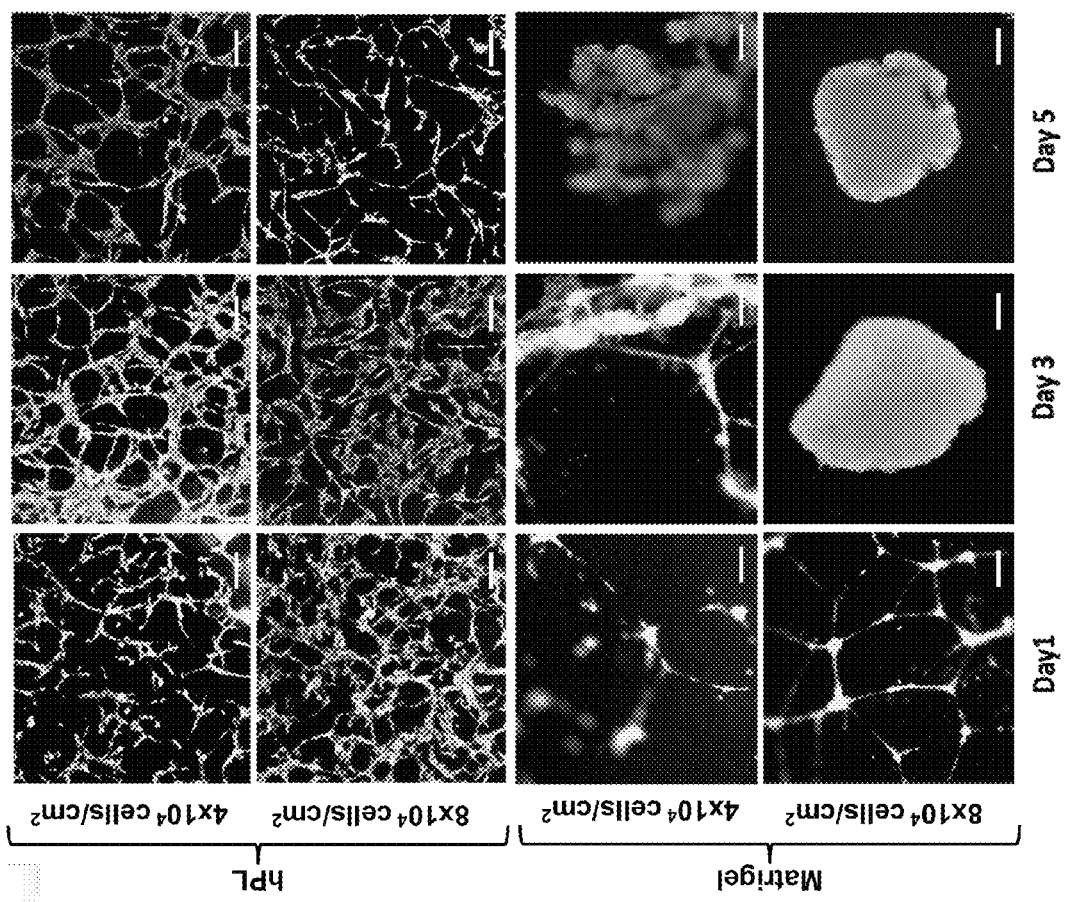

Historically, in vitro assays have little or no control over the rate and stage of angiogenesis.[9] The present data shows in vitro hPE-based angiogenesis assays can be modulated to control the maturation and morphology of angiogenic network formation by varying the initial cell seeding density. After 1 day, HUVECs seeded at density of 40,000 cells/cm$^2$ formed more defined tubules by comparison to seeding at a density of 80,000 cells/cm$^2$, but by day 5, cells seeded at both densities had well defined tubules (FIG. 3A). These results show that the maturation stage of network formation can be controlled when cultures are exposed to hPE by varying the cell seeding density. For example, a high cell seeding density results in slower maturation of angiogenic networks and would allow improved analysis of the progression of angiogenesis as network formation is extended. Whereas lower cell densities result in a faster maturation of angiogenic networks and thus allow for a more rapid screening approach, such as to test the effectiveness of angiogenesis blockers by cancer drugs.

As the historical gold standard for in vitro angiogenesis assays, Matrigel-induced angiogenic networks were compared to hPE-induced networks (FIG. 3A). Morphologies of endothelial cell capillary networks were first analyzed by exposing cell cultures to either Matrigel or hPE using Calcein AM to determine viability and network structure. One day post seeding, Matrigel coated plates had shown HUVEC to form defined angiogenic tubule networks, but after 3 d network structures collapsed into spherical balls of apoptotic cells. While some cell death was noted in hPE induced networks no apoptotic ball formations were observed after an extended 5 d period.

During the late stages of angiogenesis ECs recruit smooth muscle cells (SMC) to stabilize vessels as capillary networks mature. As such, the effect of hPE and Matrigel on smooth muscle cell morphology was assessed. Interestingly, in the absence of HUVEC, SMC seeded onto Matrigel formed tubules after 1 d (FIG. 3B.i), but on hPE coated plates maintained typical 'hill and valley' formations (FIG. 3B.ii), indicating significant differences in molecular signaling pathways between cell types. SMC are not known to form tubules in the initial stages of microvessel formation, thus these results may indicate hPE-based angiogenesis more accurately represent normal physiology.

Analysis of hPE-Induced Angiogenesis for Drug Screening Applications

Figure 4A:
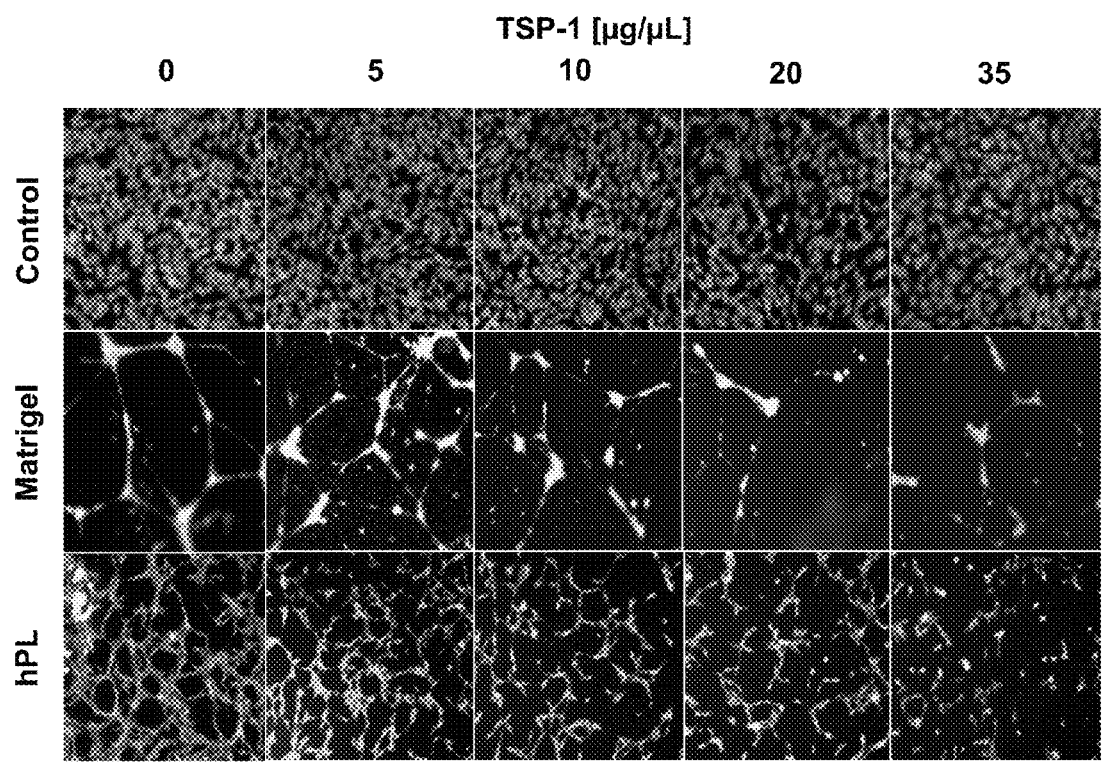
FIGS. 4A-4C illustrate screening of anti-antiangiogenic tumor suppressive protein Thrombospondin-1 using hPE-based angiogenesis screening assay.
Figure 4B:
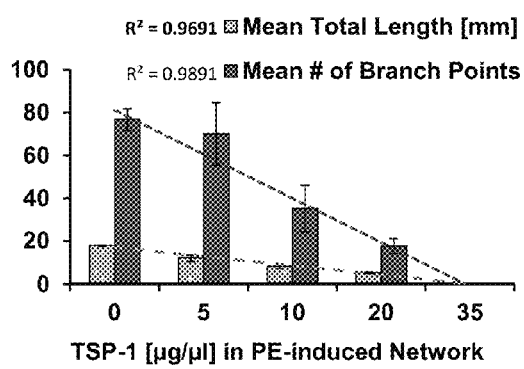
Figure 4C:
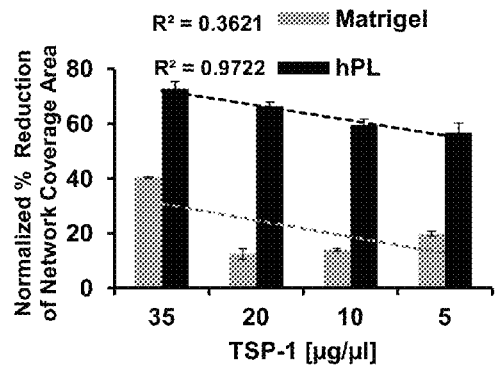

In addition to its role in regenerative medicine, angiogenesis driven by the human placental extract (hPE) was tested for its ability to screen angiogenesis related drugs in vitro. Matrigel and hPE-based angiogenesis assays were screened against thrombospondin-1 (TSP-1), a glycoprotein with potent inhibition activity on neovascularization. TSP-1 represents a model drug for the anti-angiogenic treatment of solid tumors[23]. After 1 d of culture, control HUVECs seeded directly onto tissue culture plates were not affected by TSP-1, with cells forming typical cobblestone morphologies. By contrast, HUVECs cultured on hPE treated culture plates had significantly reduced angiogenic network formation. (FIG. 4A). Results show the total tubule-length and branch points to decrease linearly as a function of TSP-1 concentration (FIG. 4B). Importantly, these studies indicate hPE-based assays to be more sensitive to drug concentration as compared to Matrigel-based assays. This is shown by the higher correlation between TSP-1 concentration and percent reduction in angiogenic network area of coverage, with $R^2$ values of 0.97 and 0.36, respectively (FIG. 4C). Additionally, because the hPE is human derived, it avoids interspecies based inaccuracies that may result from screening with non-human systems[13,14].

In Vitro Angiogenic Networks Formation Within a 3D Bioscaffold

Figure 5A:
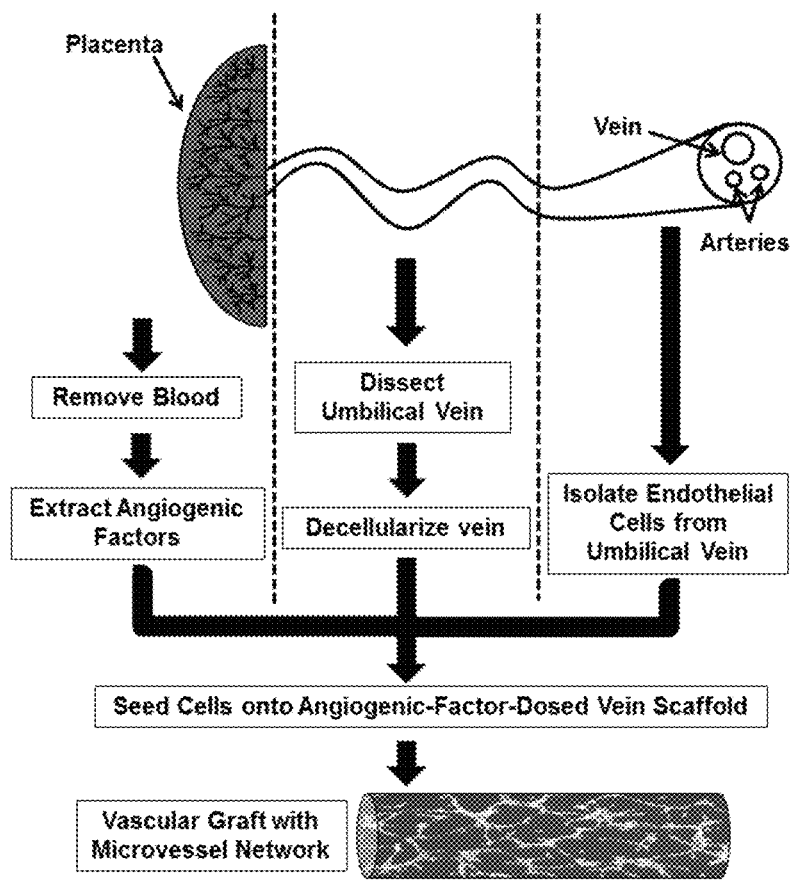
FIGS. 5A-5C illustrate in vitro angiogenesis on 3D tissue constructs.
Figure 5B:
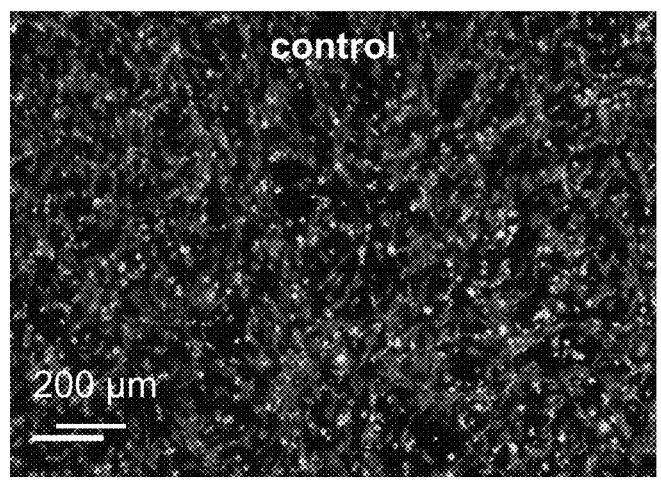

Successful vascularization of engineered organs has been a major roadblock to developing successful regenerative medicine therapies[24], the potential of hPE to induce angiogenesis in an ex vivo derived bioscaffold was analyzed. These studies show that hPE induced the formation of angiogenic networks in engineered (decellularized) human umbilical vein (HUV) bioscaffolds (FIG. 5A). Consistent with assays in 2D culture plates, endothelial cells (ECs) seeded onto the bioscaffolds developed elongated morphologies that were connected into multi-cellular cords, forming complex interconnected networks.

Figure 5C:
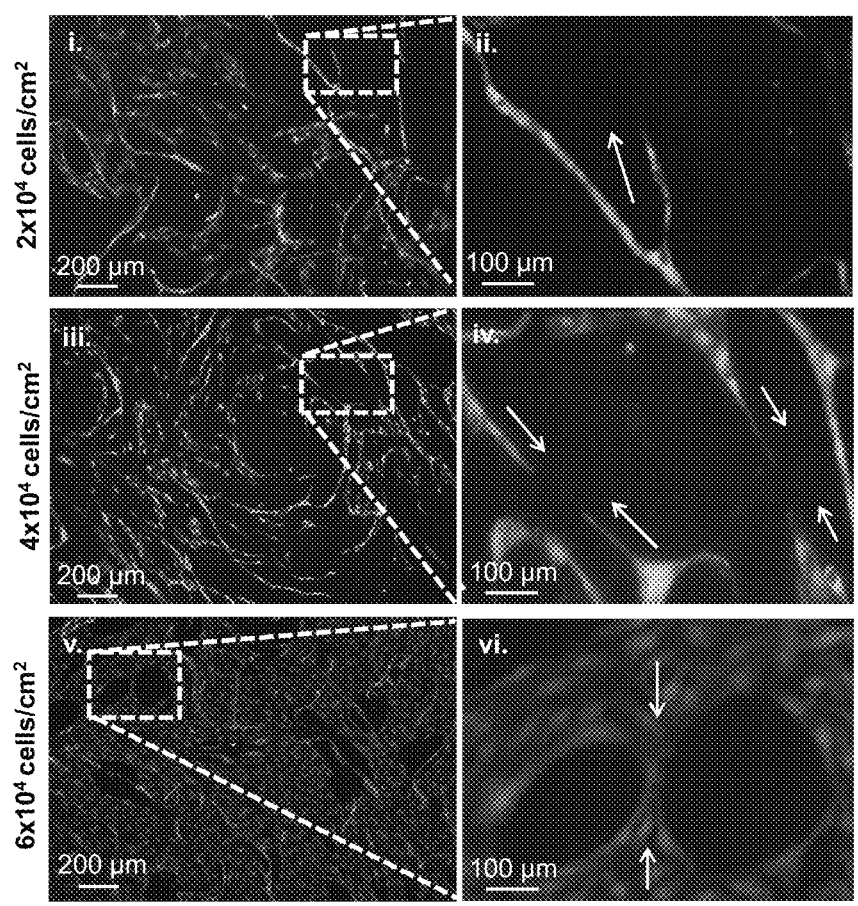

In vivo angiogenesis occurs by a variety of mechanisms, most commonly sprouting or intussusception. These data show sprouting versus intussusceptive angiogenesis can be modulated in vitro by varying cell density when incubated with hPE. At lower cell densities ($2 \times 10^4$ cells/cm$^2$) network morphologies on the hPE-incubated scaffolds exhibited sprouting angiogenesis (FIG. 5C.i, 5C.ii), at intermediate densities ($4 \times 10^4$ cells/cm$^2$) network morphologies exhibited a combination of sprouting and intussusceptive angiogenesis (FIG. 5C.iii, 5C.iv), and at higher densities ($6 \times 10^4$ cells/cm$^2$) network morphology more closely resembled intussusceptive angiogenesis (FIG. 5C.v, 5C.vi). The correlation between cell density and the specific mechanism of angiogenesis supports the current understanding of in vivo capillary and network formation, as sprouting generally occurs during early phases of angiogenesis in low cell density regions devoid of capillaries. By contrast, intussusception occurs in higher cell density regions where capillaries and endothelial cells already exist[25,26].

Induction of Angiogenesis In Vivo

Using a subcutaneous rat model (FIG. 6A) the angiogenic response to dosed scaffolds (Matrigel and hPE) was assessed 5 days post implantation. Both control and Matrigel-incubated scaffolds displayed significant fibrosis surrounding the scaffold, whereas hPE dosed scaffolds exhibited no discernible fibrosis around the implant (FIG. 6B.i-6B.iii.). Fibrosis prevention in hPE samples is believed to result from immune related molecules, as detected with LC-MS/MS, including, but not limited to, anti-inflammatory Annexins (ANXA1, ANXA2, ANXA4, and ANXA5)[27], antimicrobial defensin peptides such as DEFA1[28], and MRC1, which is know to bind to potential pathogens including viruses and bacteria.

As shown by brightfield microscopy both Matrigel and hPE-incubated scaffolds displayed a significant increase in neovascularization compared to controls (FIG. 6B.iv.-6B.vi.). While the total vascularization appeared similar, hPE treatments show the formation of maturing capillary beds, whereas Matrigel samples appeared less structured, without evidence of mature capillary bed formation. H&E stained sections show that cells had migrated into and throughout scaffolds incubated in hPE, whereas Matrigel incubated samples had reduced cellular infiltration, and cells within the control samples were limited to the scaffold periphery (FIG. 6B.vii.-6B.ix.). The improved cell migration in both Matrigel and hPE-incubated samples was the result of chemotactic and growth factor signals adsorbed to the scaffold structure. Despite improved cell migration with both hPE and Matrigel dosed scaffolds over controls, cellular remodeling between the sample groups displayed variation. Cell dense regions in the Matrigel-incubated samples displayed remnants of the original HUV fibers, with the general structure qualitatively more amorphous in comparison to hPE-incubated scaffolds that appeared to be almost completely remodeled, displaying a more organized fiber and cellular structure (FIG. 6B.vii.-6B.ix.).

Discussion

Tissue regeneration, infarct tissue and ischemic wound repair are three clinical areas where an improved strategy for wound recovery or organ replacement would have significant clinical impact. The use of amniotic and chorionic membranes in a variety of applications has grown significantly over the last 5 years, with an increasing body of evidence indicating perinatal tissues hold considerable clinical promise[29-32].

Results herein detail a novel approach to concentrate and deliver physiological ratios of a potent human derived stimulator of angiogenesis and tissue remodeling. These data show enhanced cellular activity toward initiating capillary formation (in vitro and in vivo), controlling EC phenotype during angiogenesis with a capacity to modulate growth or maturation dynamics, and a significant reduction in in vivo tissue fibrosis.

The capacity to modulate the in vitro maturation rate of capillary network formation and to control the occurrence of sprouting and intussusceptive angiogenic network morphologies may provide a useful platform to further the understanding of regulatory pathways during wound healing and organ regeneration. Based on comparisons with Matrigel, the mechanism with which hPE stimulates cells appears to be fundamentally different. SMC incubated with Matrigel initiated capillary-like formations whereas SMC exposed to the hPE retained their typical hill and valley morphology, as such the human derived hPE may provide a more representative model of physiological angiogenesis in more complex models.

A number of current methods are based on human-derived (recombinant) modulators that rely on single or discrete combinations of angiogenesis modulators[33]. While discrete combinations are useful to control variation and reduce the inherent complexity of multifarious approaches, they constrain the screening process and fail to represent the broad set of human in vivo molecular interactions that are likely to be critical when testing the potential of anti-angiogenic, tumor suppressive drugs.

The inherent complexity of hPE based models may lead to advances in the pharmaceutical industry by providing a more effective screening approach for tumor suppressive drugs. Relative to current techniques, exposure of human EC to hPE was shown to have increased sensitivity to angiogenesis inhibiting drug-concentrations (TSP-1) with lower detection limits.

hPE-based models induce angiogenesis using a broad set of human-derived molecules at near physiological ratios. It is believed that regulation of only selected molecular pathways will confine attempts to discover novel anti-angiogenesis drugs as vessel formation in vivo requires the induction of multiple metabolic pathways[34,35]. As such, a drug may modulate angiogenesis via interaction with any of these numerous pathways but may have little effect inducing competent angiogenesis when the complexity of the local environment is lacking. Results from the in vivo analysis in the present example provide further evidence that the complex PE influences numerous biochemical pathways, resulting in a broad range of effects. Data shows hPE not only displayed enhanced angiogenic properties, but was also shown to have immune reductive properties, as illustrated by reduced fibrosis within hPE dosed bioscaffolds. Given complex interconnections between angiogenesis and immunological molecular pathways[36], the molecular composition of hPE provides a suitable basis for the development of clinically applicable techniques to induce capillary formation without significant immunological and inflammatory reactions.

It appears that the positive outcomes of the above-described studies are not only related to the presence of key growth factors (GF) and gene regulators in the PE, but also their presence in physiological ratios. For example, while VEGF was upregulated in hPE-induced EC, the hPE solution contained no detectable levels. This contrasts with Matrigel (BMM) that contains active concentrations of VEGF in both the standard and GFR (growth factor reduced) version. With results herein showing more mature capillary bed formations, the presence of VEGF is only one of many contributing factors, and the presence of other regulators likely plays a key role in vascular development. Similarly, with comparison to human recombinant proteins used to initiate angiogenesis, these rely on highly concentrated (typically) single GF[37-39]. Problems have been reported with single, highly reactive GF applied clinically resulting in undesirable effects[40-42].

The hPE angiogenesis model has been validated in 2D and 3D in vitro models, as well as in vivo within bioengineered tissue implants and can be readily adapted to a variety of clinical or pharmaceutical applications. Its derivation from physiologically healthy, human vascular beds combined with its angiogenic and immune reductive properties make it unique among current angiogenesis models. The data presented here have shown hPE to play a pivotal role in a number of key clinical issues where demand for alternative, more successful, approaches are a clinical priority.

REFERENCES

1. Thurston, G., Murphy, T. J., Baluk, P., Lindsey, J. R. & McDonald, D. M. Angiogenesis in mice with chronic airway inflammation: strain-dependent differences. *Am J Pathol* 153, 1099-1112 (1998).
2. Cristofanilli, M., Charnsangavej, C. & Hortobagyi, G. N. Angiogenesis modulation in cancer research: novel clinical approaches. *Nature reviews. Drug discovery* 1, 415-426 (2002).
3. Lokmic, Z. & Mitchell, G. M. Engineering the microcirculation. *Tissue Eng Part B Rev* 14, 87-103 (2008).
4. Kurz, H., Burri, P. H. & Djonov, V. G. Angiogenesis and vascular remodeling by intussusception: from form to function. *News in physiological sciences: an international journal of physiology produced jointly by the Interna-* tional Union of Physiological Sciences and the American Physiological Society 18, 65-70 (2003).
5. Burri, P. N. & Djonov, V. Intussusceptive angiogenesis—the alternative to capillary sprouting. *Molecular aspects of medicine* 23, S1-27 (2002).
6. Risau, W. Mechanisms of angiogenesis. *Nature* 386, 671-674 (1997).
7. Folkman, J. Angiogenesis in cancer, vascular, rheumatoid and other disease. *Nature medicine* 1, 27-31 (1995).
8. Jain, R. K., Schlenger, K., Hockel, M. & Yuan, F. Quantitative angiogenesis assays: progress and problems. *Nature medicine* 3, 1203-1208 (1997).
9. Auerbach, R., Akhtar, N., Lewis, R. L. & Shinners, B. L. Angiogenesis assays: problems and pitfalls. Cancer metastasis reviews 19, 167-172 (2000).
10. Auerbach, R., Lewis, R., Shinners, B., Kubai, L. & Akhtar, N. Angiogenesis assays: a critical overview. *Clinical chemistry* 49, 32-40 (2003).
11. Kleinman, H. K. & Martin, G. R. Matrigel: basement membrane matrix with biological activity. *Seminars in cancer biology* 15, 378-386 (2005).
12. Cockerill, G. W., Gamble, J. R. & Vadas, M. A. Angiogenesis: models and modulators. *International review of cytology* 159, 113-160 (1995).
13. Warren, M. S. et al. Comparative gene expression profiles of ABC transporters in brain microvessel endothelial cells and brain in five species including human. *Pharmacological Research* 59, 404-413 (2009).
14. Febbraio, M., Najjar, D. P. & Silverstein, R. L. CD36: a class B scavenger receptor involved in angiogenesis, atherosclerosis, inflammation, and lipid metabolism. *Journal of Clinical Investigation* 108, 785-791 (2001).
15. Wang, Y. & Zhao, S. in Vascular Biology of the Placenta (San Rafael (CA); 2010).
16. Fett, J. W. et al. Isolation and characterization of angiogenin, an angiogenic protein from human carcinoma cells. *Biochemistry* 24, 5480-5486 (1985).
17. Xu, J. et al. Proteolytic exposure of a cryptic site within collagen type IV is required for angiogenesis and tumor growth in vivo. *The Journal of cell biology* 154, 1069-1080 (2001).
18. Kim, S., Bell, K., Mousa, S. A. & Varner, J. A. Regulation of Angiogenesis<i> in Vivo</i> by Ligation of Integrin α5β1 with the Central Cell-Binding Domain of Fibronectin. *The American journal of pathology* 156, 1345-1362 (2000).
19. Iozzo, R. V. & San Antonio, J. D. Heparan sulfate proteoglycans: heavy hitters in the angiogenesis arena. *Journal of Clinical Investigation* 108, 349-355 (2001).
20. Patarroyo, M., Tryggvason, K. & Virtanen, I. in Seminars in cancer biology, Vol. 12 197-207 (Elsevier, 2002).
21. Rundhaug, J. E. Matrix metalloproteinases and angiogenesis. *J Cell Mol Med* 9, 267-285 (2005).
22. Kalluri, R. Basement membranes: structure, assembly and role in tumour angiogenesis. *Nature reviews. Cancer* 3, 422-433 (2003).
23. Lawler, J. Thrombospondin-1 as an endogenous inhibitor of angiogenesis and tumor growth. *J Cell Mol Med* 6, 1-12 (2002).
24. Laschke, M. W. et al. Angiogenesis in tissue engineering: breathing life into constructed tissue substitutes. *Tissue engineering* 12, 2093-2104 (2006).
25. Adair, T. in Integrated systems physiology, from molecule to function to disease (Morgan & Claypool, 2011).
26. Djonov, V., Baum, 0. & Burri, P. H. Vascular remodeling by intussusceptive angiogenesis. *Cell and tissue research* 314, 107-117 (2003).
27. Perretti, M. et al. Endogenous lipid- and peptide-derived anti-inflammatory pathways generated with glucocorticoid and aspirin treatment activate the lipoxin A4 receptor. *Nature medicine* 8, 1296-1302 (2002).
28. Paslakis, G. et al. The Putative Role of Human Peritoneal Adipocytes in the Fight against Bacteria: Synthesis of the Antimicrobial Active Peptide DEFA1-3. *Nephron Experimental Nephrology* 115, e96-e100 (2010).
29. Lee, S.-H. & Tseng, S. Amniotic membrane transplantation for persistent epithelial defects with ulceration. *American journal of ophthalmology* 123, 303-312 (1997).
30. Jin, C. Z. et al. Human amniotic membrane as a delivery matrix for articular cartilage repair. *Tissue engineering* 13, 693-702 (2007).
31. Bose, B. Burn wound dressing with human amniotic membrane. *Annals of the Royal College of Surgeons of England* 61, 444 (1979).
32. Daniel, J., Abe, K. & McFetridge, P. S. Development of the human umbilical vein scaffold for cardiovascular tissue engineering applications. *ASAIO J* 51, 252-261 (2005).
33. Vailhe, B., Vittet, D. & Feige, J. J. In vitro models of vasculogenesis and angiogenesis. *Laboratory investigation; a journal of technical methods and pathology* 81, 439-452 (2001).
34. Pepper, M., Ferrara, N., Orci, L. & Montesano, R. Potent synergism between vascular endothelial growth factor and basic fibroblast growth factor in the induction of angiogenesis in vitro. *Biochemical and biophysical research communications* 189, 824-831 (1992).
35. Sullivan, D. C. & Bicknell, R. New molecular pathways in angiogenesis. *British journal of cancer* 89, 228-231 (2003).
36. O'Byrne, K. J., Dalgleish, A., Browning, M., Steward, W. & Harris, A. The relationship between angiogenesis and the immune response in carcinogenesis and the progression of malignant disease. *European journal of cancer* 36, 151-169 (2000).
37. Montesano, R., Vassalli, J.-D., Baird, A., Guillemin, R. & Orci, L. Basic fibroblast growth factor induces angiogenesis in vitro. *Proceedings of the National Academy of Sciences* 83, 7297-7301 (1986).
38. Ferrara, N. & Alitalo, K. Clinical applications of angiogenic growth factors and their inhibitors. *Nature medicine* 5 (1999).
39. Zisch, A. H., Lutolf, M. P. & Hubbell, J. A. Biopolymeric delivery matrices for angiogenic growth factors. *Cardiovascular Pathology* 12, 295-310 (2003).
40. Epstein, S. E., Fuchs, S., Zhou, Y. F., Baffour, R. & Kornowski, R. Therapeutic interventions for enhancing collateral development by administration of growth factors: basic principles, early results and potential hazards. *Cardiovascular Research* 49, 532-542 (2001).
41. Lee, R. J. et al. VEGF gene delivery to myocardium deleterious effects of unregulated expression. *Circulation* 102, 898-901 (2000).
42. Hariawala, M. D. et al. VEGF improves myocardial blood flow but produces EDRF-mediated hypotension in porcine hearts. *Journal of Surgical Research* 63, 77-82 (1996).

The invention claimed is:
1. A method of making a human placental extract, the method comprising:
obtaining a sample from a human placenta;
removing blood from the placental sample to produce a crude placental extract;
mixing the crude placental extract with a protein solubilization agent to solubilize and linearize proteins in the crude extract;
separating and removing solid materials from the solubilized protein-placental extract;

performing dialysis on the solubilized protein-placental extract to remove the protein solubilization agent; and after dialysis, removing remaining solids from the extract to produce the human placental extract, whereby the resulting human placental extract contains less than 2% normalized protein abundance of collagen IV or laminin.

2. The method of claim 1, wherein removing blood from the placental sample comprises homogenizing the human placenta sample with a buffer, centrifuging the homogenized sample, and discarding the supernatant containing blood.

3. The method of claim 1, wherein the protein solubilization agent is urea.

4. The method of claim 1, wherein separating solid materials from the solubilized protein-placental extract comprises centrifuging the solubilized protein-placental extract and removing solids.

5. The method of claim 1, wherein the method is conducted at a temperature between about −86° C. and about 5° C.

6. The method of claim 1, wherein removing remaining solids from the dialyzed protein-placental extract comprises centrifuging the dialyzed protein-placental extract and removing remaining solids.

7. The method of claim 1, wherein the resulting human placental extract contains less than 2% normalized protein abundance of laminin.

8. A method of making a human placental extract, the method comprising:

obtaining a sample from a human placenta;

removing blood from the placental sample to produce a crude placental extract;

mixing the crude placental extract with a protein solubilization agent to solubilize and linearize proteins in the crude extract;

separating and removing solid materials from the solubilized protein-placental extract;

performing dialysis on the solubilized protein-placental extract to remove the protein solubilization agent; and after dialysis, removing remaining solids from the extract to produce the human placental extract, whereby the resulting human placental extract contains less than 2% normalized protein abundance of collagen IV.

9. A method of making a human placental extract, the method comprising:

obtaining a sample from a human placenta;

removing blood from the placental sample to produce a crude placental extract;

mixing the crude placental extract with a protein solubilization agent to solubilize and linearize proteins in the crude extract;

separating and removing solid materials from the solubilized protein-placental extract;

performing dialysis on the solubilized protein-placental extract to remove the protein solubilization agent; and after dialysis, removing remaining solids from the extract to produce the human placental extract, whereby the resulting human placental extract contains less than 2% normalized protein abundance of collagen IV and less than 2% normalized protein abundance of laminin.

* * * * *